(12) United States Patent
Sha et al.

(10) Patent No.: US 11,541,377 B2
(45) Date of Patent: *Jan. 3, 2023

(54) MODIFIED Y-TYPE MOLECULAR SIEVE, CATALYTIC CRACKING CATALYST COMPRISING THE SAME, THEIR PREPARATION AND APPLICATION THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Hao Sha, Beijing (CN); Lingping Zhou, Beijing (CN); Shuai Yuan, Beijing (CN); Weilin Zhang, Beijing (CN); Zhenyu Chen, Beijing (CN); Mingde Xu, Beijing (CN); Huiping Tian, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 41 days.

This patent is subject to a terminal disclaimer.

(21) Appl. No.: 17/268,684

(22) PCT Filed: Aug. 20, 2019

(86) PCT No.: PCT/CN2019/101532
§ 371 (c)(1),
(2) Date: Feb. 16, 2021

(87) PCT Pub. No.: WO2020/038350
PCT Pub. Date: Feb. 27, 2020

(65) Prior Publication Data
US 2021/0170373 A1 Jun. 10, 2021

(30) Foreign Application Priority Data
Aug. 20, 2018 (CN) .......................... 201810949391.X
Aug. 20, 2018 (CN) .......................... 201810949393.9

(51) Int. Cl.
| | | |
|---|---|---|
| *B01J 29/08* | (2006.01) | |
| *B01J 37/30* | (2006.01) | |
| *C10G 11/05* | (2006.01) | |
| *B01J 37/10* | (2006.01) | |
| *B01J 21/04* | (2006.01) | |

(Continued)

(52) U.S. Cl.
CPC ............. *B01J 29/088* (2013.01); *B01J 21/04* (2013.01); *B01J 21/16* (2013.01); *B01J 35/1038* (2013.01); *B01J 35/1061* (2013.01); *B01J 35/1066* (2013.01); *B01J 37/0207* (2013.01); *B01J 37/10* (2013.01); *B01J 37/30* (2013.01); *C07C 4/06* (2013.01); *C10G 11/05* (2013.01); *B01J 2229/186* (2013.01); *B01J 2229/24* (2013.01); *B01J 2229/36* (2013.01); *B01J 2229/37* (2013.01); *C07C 2521/04* (2013.01); *C07C 2521/16* (2013.01); *C07C 2529/08* (2013.01); *C10G 2300/202* (2013.01); *C10G 2300/308* (2013.01); *C10G 2300/4006* (2013.01); *C10G 2300/4018* (2013.01); *C10G 2400/30* (2013.01)

(58) Field of Classification Search
CPC . B01J 29/088; B01J 21/04; B01J 21/16; B01J 35/1038; B01J 35/1061; B01J 35/1066; B01J 37/0207; B01J 37/10; B01J 37/30; B01J 2229/186; B01J 2229/24; B01J 2229/36; B01J 2229/37; C07C 4/06; C07C 2529/08; C10G 11/05; C10G 2300/202; C10G 2300/308; C10G 2300/4006; C10G 2300/4018; C10G 2400/30
See application file for complete search history.

(56) References Cited

U.S. PATENT DOCUMENTS

| | | |
|---|---|---|
| 5,686,374 A | 11/1997 | Nakaoka |
| 2008/0156698 A1 | 7/2008 | Hu et al. |

FOREIGN PATENT DOCUMENTS

| | | |
|---|---|---|
| CN | 1055000 A | 10/1991 |
| CN | 1098130 A | 2/1995 |

(Continued)

*Primary Examiner* — In Suk C Bullock
*Assistant Examiner* — Jason Y Chong
(74) *Attorney, Agent, or Firm* — Novick, Kim & Lee, PLLC; Allen Xue

(57) ABSTRACT

A modified Y-type molecular sieve has a rare earth content of about 4-11% by weight on the basis of rare earth oxide, a sodium content of no more than about 0.5 wt % by weight on the basis of sodium oxide, a zinc content of about 0.5-5% by weight on the basis of zinc oxide, a phosphorus content of about 0.05-10% by weight on the basis of phosphorus pentoxide, a framework silica-alumina ratio of about 7-14 calculated on the basis of $SiO_2/Al_2O_3$ molar ratio, a percentage of non-framework aluminum content to the total aluminum content of no more than about 10%, and a percentage of the pore volume of secondary pores having a pore size of 2-100 nm to the total pore volume of about 20-40%. The modified Y-type molecular sieve has a high crystallinity and a high thermal and hydrothermal stability, and is rich in secondary pores.

20 Claims, No Drawings

(51) Int. Cl.
*B01J 21/16* (2006.01)
*B01J 35/10* (2006.01)
*B01J 37/02* (2006.01)
*C07C 4/06* (2006.01)

(56) References Cited

FOREIGN PATENT DOCUMENTS

| | | | | | |
|---|---|---|---|---|---|
| CN | 1362472 | A | | 8/2002 | |
| CN | 1597850 | A | * | 3/2005 | |
| CN | 1597850 | A | | 3/2005 | |
| CN | 102553631 | A | | 7/2012 | |
| CN | 103787352 | A | | 5/2014 | |
| CN | 103923698 | A | | 7/2014 | |
| CN | 104560185 | A | | 4/2015 | |
| CN | 104560187 | A | | 4/2015 | |
| CN | 106179456 | A | * | 12/2016 | |
| CN | 107973314 | A | | 5/2018 | |
| CN | 107973315 | A | | 5/2018 | |
| CN | 108452827 | A | | 8/2018 | |
| CN | 108452832 | A | * | 8/2018 | ............. B01J 21/04 |
| CN | 108452833 | A | | 8/2018 | |
| WO | 2008001709 | A1 | | 1/2008 | |

* cited by examiner

MODIFIED Y-TYPE MOLECULAR SIEVE, CATALYTIC CRACKING CATALYST COMPRISING THE SAME, THEIR PREPARATION AND APPLICATION THEREOF

CROSS-REFERENCE TO RELATED APPLICATIONS

The present application is a US national phase entry of International Application No. PCT/CN2019/101532, filed on Aug. 20, 2019, which claims the priority of the patent application No. 201810949391.X, filed on Aug. 20, 2018, before the Chinese Patent Office, entitled "Modified Y-type molecular sieve, and preparation thereof", and the priority of the patent application No. 201810949393.9, filed on Aug. 20, 2018, before the Chinese Patent Office, entitled "Catalyst cracking catalyst for processing hydrogenated LCOs, and preparation thereof", which are hereby incorporated by reference in their entireties.

TECHNICAL FIELD

The present application relates to the field of molecular sieves and catalytic cracking, and more particularly to a modified Y-type molecular sieve, a catalytic cracking catalyst comprising the same, their preparation, and application thereof.

BACKGROUND ART

Light aromatics such as benzene, toluene and xylene (BTX) are important basic organic chemical raw materials, which are widely used in the production of polyesters, chemical fibers, etc., and there is a very strong demand of them in recent years. Light aromatics such as benzene, toluene and xylene (BTX) are mainly derived from catalytic reforming and steam cracking processes using naphtha as raw materials. Due to the shortage of naphtha raw materials, there is a large market gap in light aromatics.

Catalytic cracking light cycle oil (LCO) is an important by-product of catalytic cracking. It is produced in large quantity and rich in aromatics, especially polycyclic aromatics, and is an inferior diesel fraction. With the development of market demand environmental protection requirements, LCO is greatly restricted as a diesel blending component. The hydrocarbon composition of LCO includes paraffins, naphthenes (including a small amount of olefins) and aromatics. With different catalytic cracking feedstocks and operating severity, the hydrocarbon composition of LCO may be quite different. A main component of LCO is aromatics, which may account for a mass fraction of greater than 70%, or even about 90%, and the rest are paraffins and naphthenes.

Bicyclic aromatics, as a component having the highest content in LCO, are a typical component of LCO, and are a key component affecting the production of light aromatics by catalytic cracking. Under catalytic cracking conditions, polycyclic aromatics are hard to be converted into light aromatics via ring-opening cracking. Under hydrogenation conditions, polycyclic aromatics are more easily to be saturated into heavy monocyclic aromatics, such as alkylbenzenes and cycloalkylbenzenes (e.g. indenes, tetrahydronaphthalenes, and indenes). Such heavy monocyclic aromatics are potential components for the production of light aromatics via catalytic cracking, and can be cracked into light aromatics under catalytic cracking conditions. Therefore, LCO is a potential and inexpensive resource for the production of light aromatics. The production of light aromatics through hydrogenation-catalytic cracking technology has important value in research.

In the prior arts of Chinese Patent Application Publication Nos. CN103923698A, CN104560185A, and CN104560187A, LCO is first subjected to moderate hydrogenation, in which most of the polycyclic aromatics are saturated into hydrogenated aromatics having a cycloalkane ring and an aromatic ring, and then to cracking reaction in the presence of a catalytic cracking catalyst to produce BTX light aromatics. However, the hydrogenated aromatics obtained by the hydrogenation of LCO are poorer in cracking ability, but much higher in hydrogen transfer ability than conventional catalytic cracking feedstocks. Therefore, conventional catalytic cracking catalysts used in the prior art cannot satisfy the requirement of the catalytic cracking of hydrogenated LCOs.

Since its first use in the 1960s, Y-type molecular sieves have been the main active component of fluid catalytic cracking (FCC) catalysts. However, as crude oils become heavier, the content of polycyclic compounds in FCC feedstocks increases significantly, while their ability to diffuse in the pores of molecular sieves decreases significantly. When catalysts comprising Y-type molecular sieves as the main active component are directly used to process heavy fractions such as residual oils, the accessibility of the active center of the catalysts will become a major obstacle to the cracking of polycyclic compounds contained therein, since Y-type molecular sieves used as the main active component have a pore size of only 0.74 nm. The pore structure of molecular sieves is closely related to the cracking performance, especially for residue cracking catalysts. Secondary pores of molecular sieves can increase the accessibility of macromolecules of residual oils to the active center of catalysts, thereby improving their cracking capability for residual oils.

Hydrothermal dealuminization method is one of the most widely used methods for preparing ultra-stable molecular sieves in the industry. The method comprises firstly subjecting a NaY molecular sieve to ion-exchange with an aqueous solution containing ammonium ions to reduce the content of sodium ion in the molecular sieve, and then subjecting the ammonium ion-exchanged molecular sieve to roasting at 600-825° C. in steam atmosphere to allow it to be ultra-stabilized. The method is cost-effective and is easy to be industrialized for large-scale production, and the ultra-stable Y-type molecular sieve thus obtained is rich in secondary pores, but there is a serious loss in the crystallinity of the ultra-stable Y-type molecular sieve.

At present, the production for ultra-stable Y-type molecular sieves used in the industry is normally based on an improvement on the above-mentioned hydrothermal roasting method. A method comprising two ion-exchange stages and two roasting stages can be adopted, which aims at solving the problem of severe loss of crystallinity encountered when roasting under severe conditions by carrying out the roasting in separate stages under milder conditions. The ultra-stable Y molecular sieve thus obtained may have a certain amount of secondary pores, but the proportion of secondary pores having a relatively large pore size in the total secondary pores is low. Besides, the specific surface area and the crystallinity of the ultra-stable molecular sieves also need to be further improved.

In order to better meet the need for the production of more BTX light aromatics via catalytic cracking of hydrogenated LCOs, the object of the present application is to develop a highly stable modified molecular sieve having a high cracking activity and a relatively lower hydrogen transfer capacity as a new active component, and further develop a catalytic cracking catalyst suitable for use in the catalytic cracking of hydrogenated LCOs for producing more BTX light aromatics based on this new active component, so as to promote the cracking reaction, control the hydrogen transfer reaction, further improve the conversion efficiency of hydrogenated LCOs, and maximize the production of catalytic gasolines rich in benzene, toluene and xylene (BTX).

SUMMARY OF THE INVENTION

An object of the present application is to provide a modified Y-type molecular sieve, a catalytic cracking catalyst comprising the same, their preparation and application thereof, so that, when used in the catalytic cracking of hydrogenated light cycle oils (LCDs), a catalytic cracking catalyst prepared by using the modified Y-type molecular sieve as an active component shows a higher hydrogenated LCO conversion efficiency, a lower coke selectivity, a higher yield of gasoline rich in BTX light aromatics, and a higher total yield of ethylene and propylene.

In an aspect, the present application provides a modified Y-type molecular sieve, having a rare earth content of about 4% to about 11% by weight on the basis of rare earth oxide, a sodium content of no more than about 0.5% by weight on the basis of sodium oxide, a zinc content of about 0.5% to about 5% by weight on the basis of zinc oxide, and a phosphorus content of about 0.05% to about 10% by weight on the basis of phosphorus pentoxide, based on the weight of the modified Y-type molecular sieve on a dry basis; a framework silica-alumina ratio of about 7 to about 14 calculated on the basis of $SiO_2/Al_2O_3$ molar ratio, a percentage of non-framework aluminum content to the total aluminum content of no more than about 10%, and a percentage of the pore volume of secondary pores having a pore size of 2-100 nm to the total pore volume of about 20% to about 40%.

In another aspect, the present application provides a method for the preparation of a modified Y-type molecular sieve, comprising the steps of:

(1) contacting a NaY molecular sieve with a rare earth salt solution for ion-exchange reaction, to obtain an ion-exchanged molecular sieve;

(2) subjecting the ion-exchanged molecular sieve to a hydrothermal ultra-stabilization treatment, to obtain a hydrothermally ultra-stabilized molecular sieve;

(3) subjecting the hydrothermally ultra-stabilized molecular sieve to a gas phase ultra-stabilization treatment by contacting and reacting with gaseous $SiCl_4$, to obtain a gas phase ultra-stabilized molecular sieve;

(4) subjecting the gas phase ultra-stabilized molecular sieve to an acid treatment by contacting with an acid solution, to obtain an acid-treated molecular sieve;

(5) subjecting the acid-treated molecular sieve to phosphorus modification by contacting with a phosphorus compound, to obtain a phosphorus-modified molecular sieve; and (6) impregnating the phosphorus-modified molecular sieve with a zinc salt solution, to obtain the modified Y-type molecular sieve.

Preferably, the hydrothermal ultra-stabilization treatment of the step (2) is carried out by roasting at a temperature of about 350° C. to about 480° C. in an atmosphere comprising about 30 vol % to about 90 vol % of steam for about 4.5 h to about 7 h.

In a further aspect, the present application provides a catalytic cracking catalyst, comprising, based on the weight of the catalyst on a dry basis, about 10% to about 50% by weight of a modified Y-type molecular sieve, a binder, and clay; wherein the modified Y-type molecular sieve is a modified Y-type molecular sieve according to the present application or a modified Y-type molecular sieve obtained by the method according to the present application.

In yet another aspect, the present application provides the use of a modified Y-type molecular sieve according to the present application in the catalytic cracking of a hydrocarbon feedstock, particularly a hydrogenated light cycle oil, comprising contacting the hydrocarbon feedstock with a catalytic cracking catalyst comprising the modified Y-type molecular sieve under catalytic cracking conditions.

The modified Y-type molecular sieve provided in the present application has a high crystallinity and a high thermal and hydrothermal stability, and is rich in secondary pores.

The modified Y-type molecular sieve according to the present application can be used as an active component in catalytic cracking catalysts for the catalytic cracking of hydrogenated LCOs. When used in the processing of hydrogenated LCOs, a catalytic cracking catalyst comprising the molecular sieve as an active component shows a higher conversion efficiency of hydrogenated LCOs, a lower coke selectivity, a higher yield of gasoline rich in BTX light aromatics, and a higher total yield of ethylene and propylene.

DETAILED DESCRIPTION OF THE INVENTION

The present application will be further described in detail below with reference to embodiments thereof. It is to be understood that the embodiments described herein are merely illustrative and not restrictive.

Any numerical value (including the end values of numerical ranges) provided herein is not limited to the precise value recited, but should be interpreted as covering any value close to said precise value, such as any possible value within ±5% of said precise value. Moreover, for any numerical range provided herein, one or more new numerical ranges can be obtained by arbitrarily combining the end values of the range, an end value with a specific value provided within the range, or various specific values provided within the range. Such new numerical ranges should also be considered as being specifically disclosed herein.

Unless otherwise indicated, all terms used herein have the same meaning as commonly understood by those skilled in the art, and where the definition of a term provided herein is different from the ordinary understanding in the art, the definition provided herein shall prevail.

In the present application, except for those explicitly stated, any matter or matters not mentioned are directly applicable to those known in the art without any change. Moreover, any of the embodiments described herein can be freely combined with one or more of other embodiments described herein, and the resulting technical solution or technical idea should be considered as a part of the original disclosure or original description of the present application, while should not be considered as a new matter that has not been disclosed or anticipated herein, unless it is apparent to those skilled in the art that such a combination is obviously unreasonable.

The RIPP test methods involved in the present application can be found in "Petrochemical Analysis Methods (RIPP Test Methods)", edited by Cuiding YANG et al., Science Press, September 1990, First Edition, ISBN: 7-03-001894-X, pages 263-268, 412-415 and 424-426, which is incorporated herein by reference in its entirety.

All patent and non-patent literatures mentioned herein, including but not limited to textbooks and journal articles, are hereby incorporated by reference in their entireties.

As used herein, the terms "Y-type molecular sieve" and "Y-type zeolite" are used interchangeably, and the terms "NaY molecular sieve" and "NaY zeolite" are also used interchangeably.

As used herein, the term "secondary pores" refers to the pores having a pore size (i.e. pore diameter) of from 2 nm to 100 nm in the molecular sieve.

As used herein, the term "inorganic acid having a medium or higher strength" refers to an inorganic acid having an acid strength not lower than that of $HNO_2$ (nitrous acid), including but not limited to $HClO_4$ (perchloric acid), HI (hydrogen iodide), HBr (hydrobromic acid), HCl (hydrochloric acid), $HNO_3$ (nitric acid), $H_2SeO_4$ (selenic acid), $H_2SO_4$ (sulfuric acid), $HClO_3$ (chloric acid), $H_2SO_3$ (sulfuric acid), $H_3PO_3$ (phosphoric acid), and $HNO_2$ (nitrous acid), and the like.

As used herein, the terms "rare earth solution" and "rare earth salt solution" are used interchangeably, and are preferably an aqueous solution of a rare earth salt.

As used herein, the expression "Y-type molecular sieve having a normal lattice constant" means that the lattice constant of the Y-type molecular sieve is within the range of the lattice constant of conventional NaY molecular sieves, which is preferably in a range of about 2.465 nm to about 2.472 nm.

As used herein, the term "atmospheric pressure" means a pressure of about 1 atm.

As used herein, the weight, on a dry basis, of a material refers to the weight of the solid product obtained after calcining the material at 800° C. for 1 hour.

In the present application, unless otherwise indicated, the mass of various molecular sieves involved is calculated on a dry basis; the mass (content) of the rare earth salt and the rare earth is calculated on the basis of the mass (content) of rare earth oxide, which may also be referred to herein as the mass (content) of rare earth oxide; the mass (content) of sodium is calculated on the basis of the mass (content) of sodium oxide, which may also be referred to herein as the mass (content) of sodium oxide; the mass (content) of zinc and zinc salt is calculated on the basis of the mass (content) of zinc oxide, which may also be referred to herein as the mass (content) of zinc oxide; and the mass (content) of phosphorus is calculated on the basis of the mass (content) of phosphorus pentoxide, and may also be referred to as the mass (content) of $P_2O_5$.

In a first aspect, the present application provides a modified Y-type molecular sieve, having a rare earth content of about 4% to about 11% by weight on the basis of rare earth oxide, a sodium content of no more than about 0.5% by weight on the basis of sodium oxide, a zinc content of about 0.5% to about 5% by weight on the basis of zinc oxide, and a phosphorus content of about 0.05% to about 10% by weight on the basis of phosphorus pentoxide, based on the weight of the modified Y-type molecular sieve on a dry basis; a framework silica-alumina ratio of about 7 to about 14 calculated on the basis of $SiO_2/Al_2O_3$ molar ratio, a percentage of non-framework aluminum content to the total aluminum content of no more than about 10%, and a percentage of the pore volume of secondary pores having a pore size of 2-100 nm to the total pore volume of about 20% to about 40%.

In a preferred embodiment, the modified Y-type molecular sieve may have a framework silica-alumina ratio (i.e. $SiO_2/Al_2O_3$ molar ratio) of about 7.8-12.6, preferably about 8.5 to about 12.6, and more preferably about 8.7 to about 12.0, such as about 8.79, 10.87, 11.95, etc.

In a preferred embodiment, the modified Y-type molecular sieve may have a rare earth content (calculated on the basis of rare earth oxide) of about 4.5% to about 10% by weight, preferably about 5% to about 9% by weight, such as about 5.6 wt %, 6.3 wt %, 8.5 wt %, etc.

According to the present application, the kind and composition of the rare earth are not particularly limited. Preferably, the rare earth may comprise La, Ce, Pr or Nd, or a combination of two, three or four of them; optionally, the rare earth may further comprise a rare earth element other than La, Ce, Pr and Nd.

In a preferred embodiment, the modified Y-type molecular sieve may have a sodium content (calculated on the basis of sodium oxide) of about 0.05-0.5% by weight, preferably about 0.05-0.3% or about 0.1-0.4% by weight, and more preferably no more than about 0.2 wt %, for example, about 0.09 wt %, 0.12 wt %, 0.14 wt %, etc.

In a preferred embodiment, the modified Y-type molecular sieve may have a zinc content (calculated on the basis of zinc oxide) of about 0.1-5 wt %, preferably about 1-4 wt %, for example, about 1 wt %, 2 wt %, 4 wt %, etc.

In a preferred embodiment, the modified Y-type molecular sieve may have a phosphorus content (calculated on the basis of $P_2O_5$) of about 0.5-10 wt %, preferably about 0.1-6 wt %, and more preferably about 1-4 wt %, for example, about 1.38 wt %, 2.89 wt %, 3.55 wt %, 5 wt %, etc.

In a preferred embodiment, the modified Y-type molecular sieve may have a percentage of non-framework aluminum content to the total aluminum content of about 5-9.5%, preferably about 6-9.5%, such as about 6.5%, 8.2%, 9.3%, etc.

In a preferred embodiment, the modified Y-type molecular sieve may have a lattice constant of about 2.440 nm to about 2.455 nm, preferably about 2.441 nm to about 2.453 nm, for example about 2.442 nm, 2.443 nm, 2.445 nm, 2.45 nm, 2.451 nm, etc.

In a preferred embodiment, the modified Y-type molecular sieve may have a total pore volume of about 0.36-0.48 mL/g, preferably about 0.38-0.42 mL/g, for example about 0.384 mL/g, 0.395 mL/g, 0.4 mL/g, 0.413 mL/g, etc.

In a preferred embodiment, the modified Y-type molecular sieve may have a pore volume of secondary pores having a pore size of 2.0-100 nm of about 0.08-0.18 mL/g, preferably about 0.10-0.16 mL/g, for example, about 0.111 mL/g, 0.117 mL/g, 0.155 mL/g, etc.

In a preferred embodiment, the modified Y-type molecular sieve may have a percentage of the pore volume of secondary pores having a pore size of 2.0-100 nm to the total pore volume of about 28% to about 38%, preferably about 25% to about 35%, for example, about 28.9%, 29.62%, 37.53%, etc.

In a preferred embodiment, the modified Y-type molecular sieve is an ultra-stable Y molecular sieve rich in secondary pores, and its secondary pores having a pore size of 2-100 nm show a dual probable pore size distribution, wherein the most probable pore size of secondary pores having a relatively smaller pore size is about 2-5 nm, and the most probable pore size of secondary pores having a relatively larger pore size is about 6-20 nm, preferably about 8-18 nm.

In a preferred embodiment, the modified Y-type molecular sieve has a percentage of the total pore volume of secondary pores having a pore size of 8-100 nm to the total pore volume of secondary pores having a pore size of 2-100 nm of about 40-80%, preferably about 45-75%, more preferably about 45-55% or about 55-77%, such as about 59.81%, 68.15%, 75.21%, etc.

In a preferred embodiment, the modified Y-type molecular sieve may have a specific surface area of about 600-670 m$^2$/g, preferably about 610-670 m$^2$/g, more preferably about 640-670 m$^2$/g, and further preferably about 646-667 m$^2$/g, such as about 646 m$^2$/g, 654 m$^2$/g, 667 m$^2$/g, etc.

In a preferred embodiment, the modified Y-type molecular sieve has a lattice collapse temperature of not lower than about 1060° C., particularly about 1065-1085° C., preferably about 1067-1085° C., for example, about 1065° C., 1077° C., 1082° C., etc.

In a preferred embodiment, the ratio of B acid to L acid in the strong acid content of the modified Y-type molecular sieve is not less than about 3.50, and may be, for example, about 3.5-6.5, preferably about 3.5-6, more preferably about 3.5-5.8, and specifically about 4.51, 4.8, 4.93, 5.37, etc, as determined by pyridine adsorption infrared spectroscopy at 350° C.

In a preferred embodiment, the modified Y-type molecular sieve shows a relative crystallinity retention of about 38% or more, for example, about 38-60%, preferably about 50-60%, such as about 46%, 51.89%, 57.34%, 58%, 58.57%, etc., after aging at 800° C. under atmospheric pressure in a 100 vol % steam atmosphere for 17 hours.

In a preferred embodiment, the modified Y-type molecular sieve has a relative crystallinity of no less than about 60%, particularly no less than about 70%, preferably about 70-80%, more preferably about 70-76%, specifically about 70.4%, 71.8%, 75.4% etc.

The modified Y-type molecular sieve provided in the present application is rich in secondary pores, has a high crystallinity and a high thermal and hydrothermal stability, and can be used as an active component in catalytic cracking catalysts for the catalytic cracking of hydrogenated LCOs. When used in the processing of hydrogenated LCOs, a catalytic cracking catalyst comprising the molecular sieve as an active component shows a high LCO conversion efficiency, a lower coke selectivity, a higher yield of BTX-rich gasoline, and a higher total yield of ethylene and propylene.

In a second aspect, the present application provides a method for the preparation of a modified Y-type molecular sieve, comprising the steps of:

(1) contacting a NaY molecular sieve with a rare earth salt solution for ion-exchange reaction, to obtain an ion-exchanged molecular sieve;

(2) subjecting the ion-exchanged molecular sieve to a hydrothermal ultra-stabilization treatment, to obtain a hydrothermally ultra-stabilized molecular sieve;

(3) subjecting the hydrothermally ultra-stabilized molecular sieve to a gas phase ultra-stabilization treatment by contacting and reacting with gaseous SiCl$_4$, to obtain a gas phase ultra-stabilized molecular sieve;

(4) subjecting the gas phase ultra-stabilized molecular sieve to an acid treatment by contacting with an acid solution, to obtain an acid-treated molecular sieve;

(5) subjecting the acid-treated molecular sieve to phosphorus modification by contacting with a phosphorus compound, to obtain a phosphorus-modified molecular sieve; and (6) impregnating the phosphorus-modified molecular sieve with a zinc salt solution, to obtain the modified Y-type molecular sieve.

In a particular embodiment, the method according to the present application comprises the following steps:

(1) contacting a NaY molecular sieve with a rare earth salt solution for ion-exchange reaction, to obtain a rare earth modified Y-type molecular sieve having a normal lattice constant and a reduced sodium oxide content;

(2) subjecting the rare earth modified Y-type molecular sieve having a normal lattice constant and a reduced sodium oxide content obtained in the step (1) to a hydrothermal roasting treatment, preferably at a temperature of about 350° C. to about 480° C. in an atmosphere comprising about 30% to about 90% by volume of steam for about 4.5 hours to about 7 hours, to obtain a Y-type molecular sieve having a reduced lattice constant;

(3) subjecting the Y-type molecular sieve having a reduced lattice constant obtained in the step (2) to Si—Al isomorphous substitution by contacting and reacting with gaseous SiCl$_4$, to obtain a gas phase ultra-stabilized Y-type molecular sieve;

(4) subjecting the gas phase ultra-stabilized molecular sieve to an acid treatment by contacting with an acid solution, to obtain an acid-treated molecular sieve;

(5) subjecting the acid-treated molecular sieve to phosphorus modification by contacting with a phosphorus compound, to incorporate phosphorus into the molecular sieve, to obtain a phosphorus-modified molecular sieve; and (6) impregnating the phosphorus-modified molecular sieve with a zinc salt solution, to obtain the modified Y-type molecular sieve.

In a preferred embodiment, the step (1) further comprises contacting a NaY molecular sieve with a rare earth salt solution for ion-exchange reaction, filtering, washing, and optionally drying, to obtain a rare earth modified Y-type molecular sieve having a reduced sodium oxide content.

In a preferred embodiment, the NaY molecular sieve used in the step (1) has a lattice constant of about 2.465 nm to about 2.472 nm, a framework silica-alumina ratio (i.e. SiO$_2$/Al$_2$O$_3$ molar ratio) of about 4.5-5.2, a relative crystallinity of about 85% or more, for example, about 85-95%, and a sodium oxide content of about 13.0-13.8% by weight.

In a preferred embodiment, the rare earth modified Y-type molecular sieve having a reduced sodium oxide content obtained in the step (1) has a lattice constant of about 2.465 nm to about 2.472 nm, a sodium content of no more than about 9.5% by weight, particularly no more than about 9.0% by weight, on the basis of sodium oxide, and a rare earth content of about 4.5-13% by weight on the basis of RE$_2$O$_3$ (rare earth oxide).

In a preferred embodiment, the rare earth modified Y-type molecular sieve having a reduced sodium oxide content obtained in the step (1) may have a sodium oxide content of about 4.5-9.5 wt %, preferably about 5.5-9.5 wt %, for example, about 8.5 wt %, and a rare earth oxide content of about 5.5-13% by weight, preferably about 5.5-12% by weight.

In a preferred embodiment, the step (1) further comprises contacting a NaY molecular sieve with a rare earth salt in an aqueous solution for ion-exchange reaction, wherein the mass ratio of the NaY molecular sieve (on a dry basis), the rare earth salt (on the basis of rare earth oxide) and water is about 1:(0.01-0.18):(5-20), and the water may be deionized water.

In a preferred embodiment, the rare earth salt is a rare earth chloride and/or a rare earth nitrate. The rare earth may be any kind of rare earth, and the kind and composition thereof are not particularly limited. For example, the rare earth may be one or more of La, Ce, Pr, Nd, and mixed rare earth. Preferably, the mixed rare earth may comprise one or more of La, Ce, Pr, and Nd, and may further comprise at least one of the rare earth elements other than La, Ce, Pr, and Nd.

In a preferred embodiment, the ion-exchange reaction of the step (1) may be carried out at a temperature of about 15° C. to about 95° C., preferably about 65-95° C., such as room temperature, 60° C., 90-95° C., etc.; for a period of about 30 min to about 120 minutes, preferably about 45-90 minutes.

In a preferred embodiment, in the step (1), the NaY molecular sieve, the rare earth salt and water are mixed to form a mixture, which may be carried out by first forming a slurry of the NaY molecular sieve and water, and then adding to the slurry a rare earth salt and/or an aqueous rare earth salt solution.

In a preferred embodiment, the step (1) further comprises: mixing a NaY molecular sieve with water, adding thereto a rare earth salt and/or a rare earth salt solution under stirring to conduct an ion-exchange between rare earth ions and sodium ions, filtering, and washing; wherein the washing is performed for the purpose of washing away the exchanged sodium ions, which may be carried out using deionized water.

In a preferred embodiment, in the step (1), the NaY molecular sieve, the rare earth salt and water are formed into a mixture at a mass ratio of the NaY molecular sieve:the rare earth salt:$H_2O$ of about 1:(0.01-0.18):(5-15), and stirred at a temperature of about 15° C. to about 95° C. for about 30 min to about 120 min to conduct an ion-exchange between rare earth ions and sodium ions.

In some preferred embodiments, in the step (1), the mass ratio of the NaY molecular sieve to water may be about 1:(6-20), preferably about 1:(7-15).

In a preferred embodiment, the hydrothermal ultra-stabilization/hydrothermal roasting treatment of the step (2) comprises subjecting the ion-exchanged molecular sieve to roasting at a temperature of about 350° C. to about 480° C. in an atmosphere comprising about 30 vol % to about 90 vol % of steam (also referred to as an atmosphere of 30-90% by volume of steam or a 30-90% steam atmosphere) for about 4.5 hours to about 7 hours, preferably, subjecting the ion-exchanged molecular sieve to roasting at a temperature of about 380° C. to about 460° C. in an atmosphere of about 40 vol % to about 80 vol % of steam for about 5 hours to about 6 hours. For example, the roasting treatment can be carried out at a temperature of about 390° C., about 450° C. or about 470° C., in an atmosphere of about 50% by volume, about 70% by volume, or about 80% by volume of steam.

In some preferred embodiments, the steam atmosphere of step (2) may further comprise other gases, such as one or more of air, helium or nitrogen.

In a preferred embodiment, the molecular sieve obtained after the treatment of step (2) has a lattice constant reduced to about 2.450 nm to about 2.462 nm and a water content of less than about 1 wt %.

In a preferred embodiment, the solid content of the Y-type molecular sieve having a reduced lattice constant obtained in the step (2) is not less than about 99% by weight.

In a preferred embodiment, the step (2) further comprises drying the roasted molecular sieve to obtain a Y-type molecular sieve having a reduced lattice constant and a water content of no more than about 1% by weight.

In a preferred embodiment, in the step (3), the mass ratio of silicon tetrachloride to the hydrothermally ultra-stabilized molecular sieve (on a dry basis) may be about (0.1-0.7):1, preferably about (0.3-0.6):1, for example, about 0.25:1, 0.45:1, 0.5:1, etc.

In a preferred embodiment, in the step (3), the reaction of the molecular sieve and the silicon tetrachloride may be conducted at a temperature of about 200-650° C., preferably about 350-500° C., for example, about 400° C., 490° C., etc.

In a preferred embodiment, the reaction of the molecular sieve and the silicon tetrachloride may be conducted in the step (3) for about 10 minutes to about 5 hours. Optionally, washing and filtering may be carried out after the reaction to remove soluble by-products such as $Na^+$, $Cl^-$ and $Al^{3+}$ remaining in the molecular sieve.

In a preferred embodiment, the washing of step (3) can be carried out using water, such as deionized water under the following conditions: a mass ratio of water to the molecular sieve of about (5-20):1, preferably about (6-15):1; a washing temperature of about 30° C. to about 60° C.; and a pH of the spent washing liquid of about 2.5 to about 5.0. Normally, the washing is carried out to an extent that no free ions like $Na^+$, $Cl^-$ and $Al^{3+}$ can be detected in the spent washing liquid.

In a preferred embodiment, in the step (4), the gas phase ultra-stabilized Y-type molecular sieve obtained in the step (3) is contacted and reacted with an acid solution to perform channel cleaning (modification), which may also be referred to as acid treatment.

In a preferred embodiment, the step (4) further comprises mixing the molecular sieve obtained in the step (3) with an acid solution, and reacting for a period of time, and then separating the molecular sieve after the reaction from the acid solution, for example, by filtration, then optionally washing and optionally drying. The washing may be carried out for the purpose of removing soluble by-products such as $Na^+$, $Cl^-$ and $Al^{3+}$ remaining in the molecular sieve.

In a further preferred embodiment, in the step (4), the washing condition may comprise: a mass ratio of water to the molecular sieve of about (5-20):1, preferably about (6-15):1, a pH of the spent washing liquid of about 2.5 to about 5.0, and a washing temperature of about 30° C. to about 60° C.

In a preferred embodiment, in the step (4), the reaction of the molecular sieve and the acid solution may be conducted at a temperature of about 60-100° C., preferably about 80-99° C., more preferably about 85-98° C., further preferably about 88-98° C., such as about 90° C., 93° C., 95° C., etc.

In a preferred embodiment, in the step (4), the contact and reaction of the molecular sieve and the acid solution may be conducted for about 60 minutes or more, preferably about 60-240 minutes, further preferably about 90-180 minutes.

In a preferred embodiment, in the step (4), the mass ratio of the acid to the molecular sieve (on a dry basis) may be about (0.001-0.15):1, preferably about (0.002-0.1):1, more preferably about (0.01-0.05):1; the mass ratio of water to the molecular sieve on a dry basis is about (5-20):1, preferably about (8-15):1.

In a preferred embodiment, in the step (4), the acid comprises at least one organic acid and at least one inorganic acid. Preferably, the inorganic acid is an acid having a medium or higher strength.

In a preferred embodiment, the organic acid may be selected from the group consisting of oxalic acid, malonic acid, succinic acid (butanedioic acid), methyl succinic acid, malic acid, tartaric acid, citric acid, salicylic acid, and the like.

In a preferred embodiment, the inorganic acid having a medium or higher strength may be selected from the group consisting of phosphoric acid, hydrochloric acid, nitric acid, sulfuric acid, and the like.

In a preferred embodiment, in the step (4), the mass ratio of the organic acid to the gas phase ultra-stabilized molecular sieve may be about (0.02-0.10):1, preferably about (0.02-0.05):1 or about (0.05-0.08):1.

In a preferred embodiment, in the step (4), the mass ratio of the inorganic acid to the gas phase ultra-stabilized molecular sieve may be about (0.01-0.06):1, preferably about (0.02-0.05):1.

In a preferred embodiment, the channel cleaning of the step (4) can be carried out in two stages, in which the molecular sieve is first contacted with an inorganic acid having a medium or higher strength at a temperature of about 80-99° C., preferably about 90-98° C., for about 60-120 minutes; then the molecular sieve obtained after the treatment is contacted with an organic acid at a temperature of about 80-99° C., preferably about 90-98° C., for about 60-120 minutes.

In a preferred embodiment, the step (5) further comprises contacting and reacting the acid-treated modified Y-type molecular sieve obtained in the step (4) with a solution containing a phosphorus compound.

In a further preferred embodiment, the phosphorus compound may be one or more selected from the group consisting of phosphoric acid, ammonium phosphate, ammonium dihydrogen phosphate, diammonium hydrogen phosphate, and the like.

In a further preferred embodiment, in the step (5), the mass ratio of water in the solution to the acid-treated molecular sieve is about (2-5):1, preferably about (3-4):1.

In a preferred embodiment, in the step (5), the mass ratio of phosphorus (on the basis of $P_2O_5$) to the acid-treated molecular sieve is about (0.0005-0.10):1, preferably about (0.001-0.06):1.

In a preferred embodiment, in the step (5), the phosphorus modification may be conducted at a temperature of about 15° C. to about 100° C., preferably about 30-95° C., for a period of about 10 min to about 100 min.

In a preferred embodiment, the step (5) further comprises reacting the acid-treated modified Y-type molecular sieve with the solution at about 15° C. to about 100° C. for about 10 min to about 100 min, then filtering, and washing; wherein the washing may be carried out using water, such as deionized water, in an amount of about 5-15 times the mass of the molecular sieve.

In a preferred embodiment, the zinc salt used in the step (6) may be zinc nitrate or zinc chloride.

In a preferred embodiment, the step (6) further comprises formulating a zinc salt into a solution, wherein the weight ratio of the zinc salt used (calculated on the basis of ZnO) to the molecular sieve is about (0.5-5.0):100, and the concentration of the zinc salt solution can be about 0.020-0.080 grams per milliliter.

In a preferred embodiment, the impregnation of the step (6) can be carried out at a temperature of about 10-60° C. Optionally, the impregnated molecular sieve can be dried at a temperature of about 130° C. for about 5 hours and then calcined at a temperature of about 350-600° C. for about 1 hour to about 4 hours.

In a particular embodiment of the present application, the method for the preparation of a modified Y-type molecular sieve comprises the following steps:

(1) contacting a NaY molecular sieve with a rare earth salt solution for ion-exchange reaction, filtering and washing, to obtain a rare earth modified Y-type molecular sieve having a normal lattice constant and a reduced sodium oxide content; wherein the ion-exchange is conducted under stirred at a temperature of about 15-95° C. for about 30 min to about 120 min;

(2) subjecting the rare earth modified Y-type molecular sieve having a normal lattice constant and a reduced sodium oxide content to roasting at a temperature of about 350° C. to about 480° C. in an atmosphere comprising about 30% to about 90% by volume of steam for about 4.5 h to about 7 h, and drying, to obtain a Y-type molecular sieve having a reduced lattice constant and a water content of less than about 1% by weight, which has a lattice constant of about 2.450 nm to about 2.462 nm;

(3) contacting the Y-type molecular sieve having a reduced lattice constant and a water content of less than about 1% by weight with gaseous $SiCl_4$ vaporized by heat, with the mass ratio of $SiCl_4$:the Y-type molecular sieve having a reduced lattice constant and a water content of less than about 1% by weight (on a dry basis) being about (0.1-0.7):1, reacting at a temperature of about 200° C. to about 650° C. for about 10 minutes to about 5 hours, optionally washing and filtering, to obtain a gas phase ultra-stabilized Y-type molecular sieve;

(4) subjecting the gas phase ultra-stabilized Y-type molecular sieve obtained in the step (3) to an acid treatment, wherein the gas phase ultra-stabilized molecular sieve is first mixed with an inorganic acid having a medium or higher strength and water, and reacted at about 80-99° C. for at least about 60-120 min; then an organic acid is added, reacted at about 80-99° C. for about 60-120 min, filtered, optionally washed and optionally dried, to obtain an acid-treated Y-type molecular sieve; wherein the mass ratio of the organic acid to the molecular sieve on a dry basis is about (0.02-0.10):1, the mass ratio of the inorganic acid having a medium or higher strength to the molecular sieve on a dry basis is about (0.01-0.05):1, and the mass ratio of water to the molecular sieve is about (5-20):1;

(5) adding the acid-treated Y-type molecular sieve to a solution containing a phosphorus compound, reacting at a temperature of about 15° C. to about 100° C. for about 10 min to about 100 min, filtering, washing, and optionally drying, wherein the mass ratio of water in the solution to the molecular sieve is about 2 to about 5, and the mass ratio of phosphorus (calculated on the basis of $P_2O_5$) to the molecular sieve is about (0.005-0.10):1; and (6) subjecting the modified Y-type molecular sieve obtained in the step (5) to impregnation with a zinc salt solution at a temperature of about 10° C. to about 60° C., drying at about 130° C. for about 5 hours, and then to calcinations at about 350-600° C. for about 1 hour to about 4 hours, to obtain the modified Y-type molecular sieve.

The method for the preparation of a modified Y-type molecular sieve provided in the present application can be used to prepare a high-silica Y-type molecular sieve rich in secondary pores with high thermal stability and high hydrothermal stability, and can greatly improve the degree of ultra-stability of the molecular sieve while maintaining a high crystallinity. The modified Y-type molecular sieve obtained has a uniform distribution of aluminum, a low non-framework aluminum content, and unobstructed secondary pores.

The catalytic cracking catalyst comprising the modified Y-type molecular sieve obtained by the method according to the present application shows a high LCO conversion efficiency (i.e., a high effective conversion rate of LCO), a lower coke selectivity, a higher yield of BTX-rich gasoline, and a higher total yield of ethylene and propylene, when used in the catalytic cracking of hydrogenated LCOs.

In a third aspect, the present application provides a catalytic cracking catalyst, comprising, based on the weight of the catalyst on a dry basis, about 10% to about 50% by weight of a modified Y-type molecular sieve, a binder, and clay; wherein the modified Y-type molecular sieve is a modified Y-type molecular sieve according to the present application or a modified Y-type molecular sieve obtained by the method according to the present application.

In a preferred embodiment, the modified Y-type molecular sieve may be present in the catalyst in an amount, on a dry basis, of about 10% to about 50% by weight, preferably about 15-45% by weight, and more preferably about 25-40% by weight, for example about 25 wt %, 30 wt %, 40 wt %, etc.

In a preferred embodiment, the clay may be one or more of clays suitable for use as a component in cracking catalysts, for example selected from the group consisting of kaolin, hydrated halloysite, montmorillonite, diatomaceous earth, halloysite, soapstone, rectorite, sepiolite, attapulgite, hydrotalcite, bentonite, and the like. Preferably, the clay is present in the catalyst in an amount, on a dry basis, of about 10% to about 80% by weight, preferably about 20% to about 55% by weight or about 30% to about 50% by weight.

In a preferred embodiment, the binder is an alumina binder. Preferably, the alumina binder is present in the catalyst in an amount of about 10% to about 40% by weight, preferably about 20% to about 35% by weight.

In a preferred embodiment, the alumina binder may be one or more of various forms of alumina, hydrated alumina, and aluminum sol commonly used in cracking catalysts. For example, it may be selected from the groups consisting of γ-alumina, η-alumina, θ-alumina, χ-alumina, pseudo-boehmite, boehmite, gibbsite, Bayerite, aluminum sol, and the like, preferably pseudo-boehmite and aluminum sol.

In a preferred embodiment, the catalyst comprises about 2-15% by weight, preferably about 3-10% by weight of aluminum sol, calculated on the basis of alumina, and about 10-30% by weight, preferably about 15-25% by weight of pseudo-boehmite, calculated on the basis of alumina.

In a preferred embodiment, the catalyst may further comprise an additional molecular sieve other than the modified Y-type molecular sieve, and the additional molecular sieve may be present in an amount of about 0-40% by weight, preferably about 0-30% by weight, further preferably about 1-20% by weight, based on the mass of the catalyst on a dry basis.

In a further preferred embodiment, the additional molecular sieve may be a molecular sieve commonly used in catalytic cracking catalysts, such as one or more of zeolites having an MFI structure, Beta zeolites, other Y zeolites, and non-zeolitic molecular sieves. Preferably, the additional Y-type zeolite may be present in an amount of no more than about 40%, particularly about 0-40% by weight, preferably about 1-20% by weight, based on the mass of the catalyst on a dry basis.

In a preferred embodiment, the additional Y-type zeolite may be, for example, one or more of REY, REHY, DASY, SOY, and PSRY; the zeolite have an MFI structure may be, for example, one or more of HZSM-5, ZRP, and ZSP; the Beta zeolite is for example Hβ; the non-zeolitic molecular sieve may be, for example, one or more of aluminum phosphate molecular sieves (AlPO molecular sieves) and silicoaluminophosphate molecular sieves (SAPO molecular sieves).

The catalytic cracking catalyst provided in the present application comprises a modified Y-type molecular sieve having a high thermal and hydrothermal stability, and thus has a high hydrothermal stability. In addition, the catalytic cracking catalyst provided in the present application comprises a highly stable modified molecular sieve having both a high cracking activity and a relatively weaker hydrogen transfer ability as an active component, so that the cracking reaction can be enhanced and the hydrogen transfer reaction can be controlled. When used in the catalytic cracking of hydrogenated LCOs, the catalyst shows a high LCO conversion efficiency, a lower coke selectivity, and a higher yield of BTX-rich gasoline, and the gas product obtained comprises a higher concentration of ethylene and propylene.

In a fourth aspect, the present application provides a method for the preparation of a catalytic cracking catalyst, comprising the steps of: providing a modified Y-type molecular sieve, forming a slurry comprising the modified Y-type molecular sieve, an alumina binder, clay, and water, spray drying, optionally washing and optionally drying, to obtain the catalytic cracking catalyst, wherein said providing a modified Y-type molecular sieve comprises providing a modified Y-type molecular sieve according to the present application, or preparing a modified Y-type molecular sieve by the method according to the present application.

Except for the step of providing a modified Y-type molecular sieve, all of the steps of the method for the preparation of a catalyst according to the present application can be carried out according to the existing methods, for example, according to the methods described in Chinese Patent Application Publication Nos. CN1098130A and CN1362472A.

In the method for the preparation of a catalyst provided in the present application, the spray drying, washing and drying can be carried out according to the methods known in the prior art, and there is no special requirements in the present application.

In a fifth aspect, the present application provides the use of a modified Y-type molecular sieve according to the present application in the catalytic cracking of a hydrocarbon feedstock, particularly a hydrogenated light cycle oil, comprising contacting the hydrocarbon feedstock with a catalytic cracking catalyst comprising the modified Y-type molecular sieve under catalytic cracking conditions.

In a sixth aspect, the present application provides the use of a catalytic cracking catalyst according to the present application in the catalytic cracking of a hydrocarbon feedstock, particularly a hydrogenated light cycle oil, comprising contacting the hydrocarbon feedstock with the catalytic cracking catalyst under catalytic cracking conditions.

In a seventh aspect, the present application provides a catalytic cracking process for processing a hydrogenated light cycle oil (hydrogenated LCO) comprising a step of contacting, under catalytic cracking conditions, the hydrogenated LCO with a catalytic cracking catalyst according to the present application or a catalytic cracking catalyst comprising a modified Y-type molecular sieve according to the present application.

According to the present application, preferably, the catalytic cracking conditions may include: a reaction temperature of about 500° C. to about 610° C., a weight hourly space velocity of about 2 $h^{-1}$ to about 16 $h^{-1}$, and a catalyst-to-oil weight ratio of about 3 to about 10.

In a preferred embodiment, the hydrogenated LCO may have the following properties: a density (at 20° C.) of about 0.850-0.920 g/cm$^3$, an H content of about 10.5-12 wt %, an S content of <50 μg/g, an N content of <10 μg/g, a total aromatics content of about 70-85 wt %, and a polycyclic aromatics content of ≤15 wt %.

In some preferred embodiments, the present application provides the following technical solutions:

A1. A modified Y-type molecular sieve, having a rare earth content of about 4-11% by weight on the basis of rare earth oxide, a sodium content of no more than about 0.5% by weight on the basis of sodium oxide, a zinc content of about 0.5-5% by weight on the basis of zinc oxide, a phosphorus content of about 0.05-10 wt % on the basis of phosphorus pentoxide, a framework silica-alumina ratio of about 7 to about 14 calculated on the basis of $SiO_2/Al_2O_3$ molar ratio, a percentage of non-framework aluminum content to the total aluminum content of no more than about 10%, a percentage of the pore volume of secondary pores having a pore size of 2-100 nm to the total pore volume of about 20% to about 40%.

A2. The molecular sieve according to Item A1, wherein the total pore volume is about 0.36 mL/g to about 0.48 mL/g.

A3. The molecular sieve according to Item A1 or A2, wherein the rare earth content is about 4.5% to about 10% by weight, the sodium content is about 0.05-0.3% by weight, the phosphorus content is about 0.1% to about 6% by weight, the lattice constant is about 2.442 nm to about 2.451 nm and the framework silica-alumina ratio is about 8.5 to about 12.6.

A4. The molecular sieve according to Item A3, wherein the percentage of the non-framework aluminum content to the total aluminum content is about 5% to about 9.5%.

A5. The molecular sieve according to Item A3, wherein the percentage of the pore volume of secondary pores having a pore size of 2-100 nm to the total pore volume is about 28% to about 38%.

A6. The molecular sieve according to Item A1 or A2, wherein the ratio of B acid to L acid is not less than about 3.50, as determined by pyridine adsorption infrared spectroscopy at 350° C.

A7. A method for the preparation of a modified Y-type molecular sieve, comprising the following steps:
(1) subjecting a NaY molecular sieve to ion-exchange with a rare earth salt solution;
(2) subjecting the ion-exchanged molecular sieve to roasting;
(3) reacting the hydrothermally ultra-stabilized molecular sieve with silicon tetrachloride;
(4) subjecting the molecular sieve reacted with silicon tetrachloride to an acid treatment;
(5) subjecting the acid-treated molecular sieve to phosphorus modification; and
(6) impregnating the phosphorus-modified molecular sieve with a zinc salt solution.

A8. The method according to Item A7, wherein in the step (1), the ion-exchange is carried out at a temperature of about 15° C. to about 95° C. for about 30 min to about 120 minutes, wherein the mass ratio of the NaY molecular sieve, the rare earth salt, and water is about 1:(0.01-0.18):(5-20), the mass of the NaY molecular sieve is calculated on a dry basis, and the mass of the rare earth salt is calculated on the basis of rare earth oxide.

A9. The method according to Item A7, wherein the roasting of the step (2) is carried out at 350-480° C. in an atmosphere comprising about 30% to about 90% by volume of steam for about 4.5 h to about 7 h.

A10. The method according to Item A7, wherein, in the step (3), the reaction temperature is about 200° C. to 650° C., the reaction time is about 10 minutes to about 5 hours, and the mass ratio of silicon tetrachloride to the hydrothermally ultra-stabilized molecular sieve is about (0.1-0.7):1, wherein the mass of the hydrothermally ultra-stabilized molecular sieve is calculated on a dry basis.

A11. The method according to Item A7, wherein, in the step (4), the acid treatment is carried out at a temperature of about 60-100° C. for about 1 hour to about 4 hours.

A12. The method according to Item A7, wherein the acid treatment comprises reacting the gas phase ultra-stabilized molecular sieve with an acid in water, wherein the mass ratio of the acid to the gas phase ultra-stabilized molecular sieve is about (0.001-0.15):1, the mass ratio of water to the gas phase ultra-stabilized molecular sieve is about (5-20):1, and the mass of the gas phase ultra-stabilized molecular sieve is calculated on a dry basis.

A13. The method according to Item A12, wherein the acid comprises one or more of organic acids and inorganic acids, and the mass ratio of the inorganic acid to the gas phase ultra-stabilized molecular sieve is about (0.001-0.05):1, and the mass ratio of the organic acid to the gas phase ultra-stabilized molecular sieve is about (0.02-0.10):1.

A14. The method according to Item A13, wherein the organic acid is one or more selected from the group consisting of oxalic acid, malonic acid, succinic acid, methyl succinic acid, malic acid, tartaric acid, citric acid, and salicylic acid; and the inorganic acid is one or more selected from the group consisting of phosphoric acid, hydrochloric acid, nitric acid, and sulfuric acid.

A15. The method according to Item A7, wherein, in the step (5), the phosphorus modification is conducted at a temperature of about 15° C. to about 100° C. for a period of about 10 min to about 100 min.

A16. The method according to Item A7, wherein in the step (5), the phosphorus compound used for the phosphorus modification is one or more selected from the group consisting of phosphoric acid, ammonium phosphate, ammonium dihydrogen phosphate, and diammonium hydrogen phosphate.

A17. The method according to Item A7, wherein the step (6) comprises subjecting the impregnated molecular sieve to calcination, wherein the impregnation temperature is about 10-60° C., the calcination temperature is about 350-600° C., and the calcination time is about 1-4 hours.

B1. A catalytic cracking catalyst for processing hydrogenated LCOs, comprising a modified Y-type molecular sieve having a rare earth content of about 4-11% by weight on the basis of rare earth oxide, a sodium content of no more than about 0.5% by weight on the basis of sodium oxide, a zinc content of about 0.5-5% by weight on the basis of zinc oxide, a phosphorus content of about 0.05-10 wt % on the basis of phosphorus pentoxide, a framework silica-alumina ratio of about 7 to about 14 calculated on the basis of $SiO_2/Al_2O_3$ molar ratio, a percentage of non-framework aluminum content to the total aluminum content of no more than about 10%, a percentage of the pore volume of secondary pores having a pore size of 2-100 nm to the total pore volume of about 20% to about 40%.

B2. The catalyst according to Item B1, wherein the modified Y-type molecular sieve has a total pore volume of about 0.36 mL/g to about 0.48 mL/g.

B3. The catalyst according to Item B1, wherein, in the modified Y-type molecular sieve, the rare earth content is about 4.5% to about 10% by weight, the sodium content is about 0.05-0.3% by weight, the zinc content is about 0.1-5% by weight, the phosphorus content is about 0.1-6 wt %, the lattice constant is about 2.442 nm to about 2.451 nm, and the framework silica-alumina ratio is about 8.5 to about 12.6.

B4. The catalyst according to Item B1, wherein, in the modified Y-type molecular sieve, the percentage of the non-framework aluminum content to the total aluminum content is about 5% to about 9.5%.

B5. The catalyst according to Item B1, wherein, in the modified Y-type molecular sieve, the percentage of the pore volume of secondary pores having a pore size of 2-100 nm to the total pore volume is about 28% to about 38%.

B6. The catalyst according to Item B1 or B2, wherein, in the modified Y-type molecular sieve, the ratio of B acid to L acid is not less than about 3.50, as determined by pyridine adsorption infrared spectroscopy at 350° C.

B7. The catalyst according to Item B1, comprising about 10% to about 50% by weight of said modified Y-type molecular sieve, a binder and clay.

B8. A method for the preparation of a catalytic cracking catalyst for processing a hydrogenated LCO, comprising the step of preparing an active component of a modified Y-type molecular sieve, wherein the step of preparing an active component of a modified Y-type molecular sieve comprises:
(1) subjecting a NaY molecular sieve to ion-exchange with a rare earth salt solution;
(2) subjecting the ion-exchanged molecular sieve to roasting;
(3) reacting the hydrothermally ultra-stabilized molecular sieve with silicon tetrachloride;
(4) subjecting the molecular sieve reacted with silicon tetrachloride to an acid treatment;
(5) subjecting the acid-treated molecular sieve to phosphorus modification; and
(6) impregnating the phosphorus-modified molecular sieve with a zinc salt solution.

B9. The method according to Item B8, wherein in the step (1), the ion-exchange is carried out at a temperature of about 15° C. to about 95° C. for about 30 min to about 120 min, wherein the mass ratio of the NaY molecular sieve, the rare earth salt, and water is about 1:(0.01-0.18):(5-20), the mass of the NaY molecular sieve is calculated on a dry basis, and the mass of the rare earth salt is calculated on the basis of rare earth oxide.

B10. The method according to Item B8, wherein the roasting of the step (2) is carried out at 350-480° C. in an atmosphere comprising about 30% to about 90% by volume of steam for about 4.5 h to about 7 h.

B11. The method according to Item B8, wherein, in the step (3), the reaction temperature is about 200° C. to about 650° C., the reaction time is about 10 minutes to about 5 hours, and the mass ratio of silicon tetrachloride to the hydrothermally ultra-stabilized molecular sieve is about (0.1-0.7):1, wherein the mass of the hydrothermally ultra-stabilized molecular sieve is calculated on a dry basis.

B12. The method according to Item B8, wherein in the step (4), the acid treatment is carried out at a temperature of about 60-100° C. for about 1 hour to about 4 hours.

B13. The method according to Item B8, wherein the acid treatment comprises reacting the gas phase ultra-stabilized molecular sieve with an acid in water, wherein the mass ratio of the acid to the gas phase ultra-stabilized molecular sieve is about (0.001-0.15):1, the mass ratio of water to the gas phase ultra-stabilized molecular sieve is about (5-20):1, and the mass of the gas phase ultra-stabilized molecular sieve is calculated on a dry basis.

B14. The method according to Item B13, wherein the acid comprises one or more of organic acids and inorganic acids, and the mass ratio of the inorganic acid to the gas phase ultra-stabilized molecular sieve is about (0.001-0.05):1, the mass ratio of the organic acid to the gas phase ultra-stabilized molecular sieve is about (0.02-0.10):1.

B15. The method according to Item B14, wherein the organic acid is one or more selected from the group consisting of oxalic acid, malonic acid, succinic acid, methyl succinic acid, malic acid, tartaric acid, citric acid, and salicylic acid; and the inorganic acid is one or more selected from the group consisting of phosphoric acid, hydrochloric acid, nitric acid, and sulfuric acid.

B16. The method according to Item B8, wherein, in the step (5), the phosphorus modification is conducted at a temperature of about 15° C. to about 100° C. for a period of about 10 min to about 100 min.

B17. The method according to Item B8, wherein in the step (5), the phosphorus compound used for the phosphorus modification is one or more selected from the group consisting of phosphoric acid, ammonium phosphate, ammonium dihydrogen phosphate, and diammonium hydrogen phosphate.

B18. The method according to Item B8, wherein the step (6) comprises subjecting the impregnated molecular sieve to calcination, wherein the impregnation temperature is about 10-60° C., the calcination temperature is about 350-600° C., and the calcination time is about 1-4 hours.

B19. The method according to any one of Items B8 to B18, comprising forming a slurry comprising about 10-50% by weight of the modified Y-type molecular sieve, a binder, clay and water, and spray drying, to obtain the catalyst.

B20. A catalytic cracking process for processing a hydrogenated LCO, comprising the step of contacting a hydrogenated LCO with the catalyst according to any one of Items B1 to B7 under catalytic cracking conditions; wherein the catalytic cracking conditions include: a reaction temperature of about 500-610° C., a weight hourly space velocity of about 2 h$^{-1}$ to about 16 h$^{-1}$, and a catalyst-to-oil weight ratio of about 3 to about 10.

EXAMPLES

The present application will be further illustrated by the following examples, without however limiting the present invention.

Raw Materials

In the following examples and comparative examples, NaY molecular sieves (also referred to as NaY zeolites) are supplied by Qilu Branch of Sinopec Catalyst Co., Ltd., of which the sodium oxide content is 13.5% by weight, the framework silica-alumina ratio (i.e. $SiO_2/Al_2O_3$ molar ratio) is 4.6, the lattice constant is 2.470 nm, and the relative crystallinity is 90%.

Rare earth chloride, and rare earth nitrate are chemically pure reagents produced by Beijing Chemical Plant; zinc nitrate and zinc chloride are chemically pure reagents produced by Beijing Chemical Plant; pseudo-boehmite is an industrial product produced by Shandong Aluminum Plant with a solid content of 61% by weight; kaolin is a kaolin specialized for cracking catalysts produced by China Kaolin Clay Co., Ltd. of Suzhou with a solid content of 76% by weight; aluminum sol is supplied by Qilu Branch of Sinopec Catalyst Co., Ltd. having an alumina content of 21% by weight.

Unless otherwise stated, the reagents used in each of the comparative examples and examples were commercially available, chemically pure reagents.

Analytical Method

In each of the comparative examples and examples, the element content of the molecular sieve was determined by X-ray fluorescence spectrometry.

The lattice constant and relative crystallinity of the molecular sieve were determined by X-ray powder diffraction (XRD) according to the RIPP 145-90, RIPP 146-90 standard methods (see "Petrochemical Analysis Methods (RIPP Test Methods)", edited by Cuiding YANG et al., Science Press, September 1990, pp. 412-415).

The framework silica-alumina ratio of the molecular sieve was calculated according to the following equation:

Framework $SiO_2/Al_2O_3$ molar ratio=$(2.5858-a_0)\times 2/(a_0-2.4191)$, wherein $a_0$ refers to the lattice constant of which the unit is nm.

The total silica-alumina ratio of the molecular sieve was calculated based on the content of Si and Al elements determined by X-ray fluorescence spectrometry. The percentage of the framework Al content to the total Al content was calculated based on the framework silica-alumina ratio determined by XRD and the total silica-alumina ratio determined by XRF, and then the percentage of non-framework Al content to the total Al content was calculated.

The lattice collapse temperature was determined by differential thermal analysis (DTA).

In each of the comparative examples and examples, the acid center type of the molecular sieve and the acid content thereof were determined by pyridine adsorption infrared spectroscopy. The instrument was IFS113V type FT-IR (Fourier transform infrared) spectrometer of Bruker Company, USA. The method for determining the acid content by pyridine adsorption infrared spectroscopy at 350° C. was as follows: a self-supported sample tablet was placed in an in-situ cell of an infrared spectrometer and sealed; the sample was heated to a temperature of 400° C., vacuumed to $10^{-3}$ Pa, and maintained at the temperature for 2 h to remove the gas molecules adsorbed by the sample; the sample was cooled to room temperature, a pyridine vapor at a pressure of 2.67 Pa was introduced, and the sample was maintained under such conditions for 30 min to achieve an adsorption equilibrium; then the sample was heated to a temperature of 350° C., and vacuumed to $10^{-3}$ Pa for desorption for 30 min; after that, the sample was cooled to room temperature and subjected to spectrographic analysis at a scanning wave number range of 1400 $cm^{-1}$ to 1700 $cm^{-1}$, and the pyridine adsorption infrared spectrum of the sample desorbed at 350° C. was obtained. The relative amount of strong Brönsted acid center (B acid center) and strong Lewis acid center (L acid center) in the molecular sieve was obtained based on the intensity of the characteristic adsorption peaks at 1540 $cm^{-1}$ and 1450 $cm^{-1}$ in the pyridine adsorption infrared spectrum.

In each of the comparative examples and examples, the method for determining the pore volume of secondary pores was as follows: according to the RIPP 151-90 standard method (see "Petrochemical Analysis Methods (RIPP Test Methods)", Cuiding YANG et al., Science Press, September 1990, pp. 424-426), the total pore volume of the molecular sieve was determined based on the adsorption isotherm, and then the micropore volume of the molecular sieve was determined based on the adsorption isotherm according to the T-plot method, and the pore volume of secondary pores was obtained by subtracting the micropore volume from the total pore volume.

The following Examples 1-3 are directed to the preparation of the modified Y-type molecular sieve and the catalytic cracking catalyst according to the present application.

Example 1

2000 kg (weight on a dry basis) NaY molecular sieve having a framework $SiO_2/Al_2O_3$ of 4.6 (sodium oxide content of 13.5% by weight, produced by Qilu Branch of Sinopec Catalyst Co., Ltd.) was added to a primary exchange tank containing 20 $m^3$ of water and stirred evenly at 25° C. Then, 600 L of $RECl_3$ solution (the rare earth concentration calculated on the basis of $RE_2O_3$ in the $RECl_3$ solution was 319 g/L, and RE was mixed rare earth of La and Ce, with the mass ratio of $La_2O_3:Ce_2O_3$ calculated on the basis of rare earth oxides being 3:2) was added, stirred for 60 minutes, filtered and washed, and the filter cake was continuously sent to a flash drying oven for drying; a rare earth modified Y-type molecular sieve having a normal lattice constant and a reduced sodium oxide content was obtained, which had a sodium oxide content of 7.0% by weight, and a lattice constant of 2.471 nm.

Then, the rare earth modified Y-type molecular sieve having a normal lattice constant and a reduced sodium oxide content was sent to a roaster for modification by roasting at a controlled temperature of 390° C. in an atmosphere of 50% steam (an atmosphere comprising 50% by volume of steam) for 6 hours; then, the molecular sieve material was introduced into a roaster for roasting and drying at a controlled temperature of 500° C. in a dry air atmosphere (comprising less than 1% by volume of steam) for 2.5 h, to obtain a Y-type molecular sieve having a reduced lattice constant and a water content of less than 1% by weight, of which the lattice constant was 2.455 nm.

Then, the Y-type molecular sieve material having a reduced lattice constant was directly sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method disclosed in Example 1 of the Patent Application Publication No. CN 103787352 A under the following conditions: the mass ratio of $SiCl_4$:Y molecular sieve was 0.5:1, the feed rate of the molecular sieve was 800 kg/h, and the reaction temperature was 400° C.

The molecular sieve material obtained after the gas phase ultra-stabilization was separated by a gas-solid separator, sent to a secondary exchange tank containing 20 $m^3$ of water added in advance, and stirred evenly. The mass of the molecular sieve material added to the secondary exchange tank was 2000 kg (weight on a dry basis). Thereafter, 0.6 $m^3$ of 10 wt % hydrochloric acid was slowly added, the reaction mixture was heated to 90° C., and stirring was continued for 60 minutes; then, 140 kg of citric acid was added, and stirring was continued at 90° C. for 60 minutes, followed by filtering and washing.

After that, the acid-treated molecular sieve cake was directly added to a solution containing ammonium phosphate, with the molecular sieve being added in an amount such that the mass ratio of phosphorus (on the basis of $P_2O_5$) to the molecular sieve was 0.04:1, and the mass ratio of water to the molecular sieve was 2.5:1, and the reaction was conducted at 50° C. for 60 min, followed by filtering and washing.

2300 ml of 0.020 g/ml $Zn(NO_3)_2$ solution was slowly added to the filter cake obtained to conduct an impregnation for 4 hours, and the impregnated molecular sieve was first dried at 130° C. for 5 hours, and then calcined at 400° C. for 3 hours, to obtain a modified ultra-stable Y-type molecular sieve containing rare earth, phosphorus and zinc, which was rich in secondary pores and designated as SZ-1.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of SZ-1.

After SZ-1 was aged in a bare state at 800° C. under atmospheric pressure in an atmosphere of 100 vol % steam for 17 h, the relative crystallinity of the molecular sieve SZ-1 before and after aging was analyzed by XRD, and the relative crystallinity retention after aging was calculated. The results are shown in Table 2, in which:

$$\text{Relative crystallinity retention} = \frac{\text{Relative crystallinity of aged sample}}{\text{Relative crystallinity of fresh sample}} \times 100$$

714.5 g of an aluminum sol having an alumina content of 21% by weight was added to 1565.5 g of deionized water, stirring was started, and 2763 g of kaolin having a solid content of 76% by weight was added and dispersed for 60 minutes. 2049 g of pseudo-boehmite having an alumina content of 61% by weight was added to 8146 g of deionized water, and 210 ml of chemically pure hydrochloric acid (HCl concentration 36 wt %) was added under stirring. After acidification for 60 minutes, the dispersed kaolin slurry was added, then 1500 g (dry basis) of finely ground SZ-1 molecular sieve was added, and stirred evenly, followed by spray drying, washing, and drying to obtain a catalyst, designated as SC-1.

The SC-1 catalyst thus obtained comprised, on a dry basis, 30% by weight of SZ-1 molecular sieve, 42% by weight of kaolin, 25% by weight of pseudo-boehmite, and 3% by weight of aluminum sol.

Example 2

2000 kg (weight on a dry basis) NaY molecular sieve with a framework $SiO_2/Al_2O_3$ of 4.6 (sodium oxide content of 13.5 wt %, produced by Qilu Branch of Sinopec Catalyst Co., Ltd.) was added to a primary exchange tank containing 20 m³ of deionized water, and stirred evenly at 90° C. Then, 800 L of $RECl_3$ solution (the rare earth concentration calculated on the basis of $RE_2O_3$ in the $RECl_3$ solution was 319 g/L, and RE was mixed rare earth of La and Ce, with the mass ratio of $La_2O_3:Ce_2O_3$ calculated on the basis of rare earth oxides being 3:2) was added, stirred for 60 minutes, filtered and washed, and the filter cake was sent to a flash drying oven for drying; a rare earth modified Y-type molecular sieve having a normal lattice constant and a reduced sodium oxide content was obtained, which had a sodium oxide content of 5.5 wt %, and a lattice constant of 2.471 nm.

Then, the rare earth modified Y-type molecular sieve having a normal lattice constant and a reduced sodium oxide content was sent to a roaster, and roasted at a temperature (atmosphere temperature) of 450° C. in a 80% steam atmosphere for 5.5 hours; then, the molecular sieve material was introduced into a roaster for roasting and drying at a controlled temperature of 500° C. in a dry air atmosphere for 2 h, to obtain a Y-type molecular sieve having a reduced lattice constant and a water content of less than 1% by weight, of which the lattice constant was 2.461 nm.

Then, the Y-type molecular sieve having a reduced lattice constant was directly sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method disclosed in Example 1 of the Patent Application Publication No. CN 103787352 A under the following conditions: a mass ratio of $SiCl_4$:Y molecular sieve of 0.25:1, a molecular sieve feed rate of 800 kg/h, and a reaction temperature of 490° C.

The molecular sieve material obtained after the gas phase ultra-stabilization was separated by a gas-solid separator and sent to a secondary exchange tank containing 20 m³ of water added in advance, and stirred evenly. The mass of the molecular sieve material added to the secondary exchange tank was 2000 kg (weight on a dry basis). Thereafter, 0.9 m³ of 7 wt % sulfuric acid solution was slowly added, and the reaction mixture was heated to 93° C., followed by stirring for 80 min; then, 70 kg of citric acid and 50 kg of tartaric acid were added, and stirring was continued at 93° C. for 70 min, followed by filtering and washing.

Then, the acid-treated molecular sieve cake was directly added to a solution containing diammonium hydrogen phosphate, with the molecular sieve being added in an amount such that the mass ratio of phosphorus (on the basis of $P_2O_5$) to the molecular sieve was 0.03:1, and the mass ratio of water to the molecular sieve was 3.0:1, and the reaction was conducted at 60° C. for 50 min, followed by filtering and washing.

Then, 2300 ml of 0.030 g/ml $ZnCl_2$ solution was slowly added to the filter cake obtained to conduct an impregnation for 4 hours, and the impregnated molecular sieve was first dried at 130° C. for 5 hours, then calcined at 380° C. for 3.5 hours, to obtain a modified ultra-stable Y molecular sieve containing rare earth, phosphorus and zinc, which was rich in secondary pores and designated as SZ-2.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of SZ-2.

After SZ-2 was aged in a bare state at 800° C. in an atmosphere of 100 vol % steam for 17 h, the crystallinity of the molecular sieve SZ-2 before and after aging was analyzed by XRD, and the relative crystallinity retention after aging was calculated. The results are shown in Table 2.

714.5 g of an aluminum sol having an alumina content of 21% by mass was added to 1565.5 g of deionized water, stirring was started, and 2763 g of kaolin having a solid content of 76 wt % was added and dispersed for 60 minutes. 2049 g of pseudo-boehmite having an alumina content of 61 wt % was added to 8146 g of deionized water, and 210 ml of chemically pure hydrochloric acid (HCl concentration 36 wt %) was added under stirring. After acidification for 60 minutes, the dispersed kaolin slurry was added, then 1500 g (dry basis) of finely ground SZ-2 molecular sieve was added, and stirred evenly, followed by spray drying, washing, and drying to obtain a catalyst, designated as SC-2.

The SC-2 catalyst obtained comprised 30% by weight of SZ-2 molecular sieve, 42% by weight of kaolin, 25% by weight of pseudo-boehmite, and 3% by weight of aluminum sol.

Example 3

2000 kg (weight on a dry basis) of NaY molecular sieve with a framework $SiO_2/Al_2O_3$ of 4.6 (sodium oxide content of 13.5% by weight, produced by Qilu Branch of Sinopec Catalyst Co., Ltd.) was added to a primary exchange tank containing 20 m³ of deionized water, and stirred evenly at 95° C. Then, 570 L of $RECl_3$ solution (the rare earth concentration calculated on the basis of $RE_2O_3$ in the $RECl_3$ solution was 319 g/L, and RE was mixed rare earth of La and Ce, with the mass ratio of $La_2O_3:Ce_2O_3$ calculated on the basis of rare earth oxides being 3:2) was added, stirred for 60 minutes, filtered and washed, and the filter cake was continuously sent to a flash drying oven for drying; a rare earth modified Y-type molecular sieve having a normal lattice constant and a reduced sodium oxide content was obtained, which had a sodium oxide content of 7.5% by weight, and a lattice constant of 2.471 nm.

Then, the rare earth modified Y-type molecular sieve having a normal lattice constant and a reduced sodium oxide content was sent to a roaster for hydrothermal modification by roasting at a temperature of 470° C. in an atmosphere comprising 70% by volume of steam for 5 h; then, the molecular sieve material was introduced into a roaster for roasting and drying at a controlled temperature of 500° C. in a dry air atmosphere for 1.5 h, to obtain a Y-type molecular sieve having a reduced lattice constant and a water content of less than 1% by weight, of which the lattice constant was 2.458 nm.

Then, the Y-type molecular sieve material having a reduced lattice constant was sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method disclosed in Example 1 of the Patent Application Publication No. CN 103787352 A under the following conditions: the mass ratio of $SiCl_4$:Y-type molecular sieve was 0.45:1, the feed rate of the molecular sieve was 800 kg/h and the reaction temperature was 400° C.

The molecular sieve material obtained after the gas phase ultra-stabilization was separated by a gas-solid separator and sent to a secondary exchange tank containing 20 m³ of deionized water added in advance, and stirred evenly. The mass of the molecular sieve material added to the secondary exchange tank was 2000 kg (weight on a dry basis). Thereafter, 1.2 m³ of 5 wt % nitric acid solution was slowly added, and the reaction mixture was heated to 95° C., and stirred for 90 minutes; then, 90 kg of citric acid and 40 kg of oxalic acid were added, and the mixture was stirred at 93° C. for 70 minutes, and then filtered and washed.

The acid-treated molecular sieve cake was directly added to a solution containing ammonium phosphate, with the molecular sieve being added in an amount such that the mass ratio of phosphorus (on the basis of $P_2O_5$) to the molecular sieve was 0.015:1, and the mass ratio of water to the molecular sieve was 2.8:1, and the reaction was conducted at 70° C. for 30 min, followed by filtering and washing.

Then, 2500 ml of 0.070 g/ml $Zn(NO_3)_2$ solution was slowly added to the filter cake obtained to conduct an impregnation for 4 hours. The impregnated molecular sieve was first dried at 130° C. for 5 hours, and then calcined at 500° C. for 2 hours, to obtain a modified ultra-stable Y molecular sieve containing rare earth, phosphorus and zinc, which was rich in secondary pores and designated as SZ-3.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of SZ-3.

After SZ-3 was aged in a bare state at 800° C. in an atmosphere of 100 vol % steam for 17 h, the crystallinity of the molecular sieve SZ3 before and after aging was analyzed by XRD, and the relative crystallinity retention after aging was calculated. The results are shown in Table 2.

714.5 g of an aluminum sol having an alumina content of 21% by weight was added to 1565.5 g of deionized water, stirring was started, and 2763 g of kaolin having a solid content of 76 wt % was added and dispersed for 60 minutes. 2049 g of pseudo-boehmite having an alumina content of 61 wt % was added to 8146 g of deionized water, and 210 ml of chemically pure hydrochloric acid (HCl concentration 36 wt %) was added under stirring. After acidification for 60 minutes, the dispersed kaolin slurry was added, then 1500 g (dry basis) of finely ground SZ-3 molecular sieve was added, and stirred evenly, followed by spray drying, washing, and drying, to obtain a catalyst, designated as SC-3.

The SC-3 catalyst obtained comprised 30% by weight of SZ-3 molecular sieve, 42% by weight of kaolin, 25% by weight of pseudo-boehmite, and 3% by weight of aluminum sol.

The following Comparative Examples 1-3 are directed to the preparation of modified Y-type molecular sieves and catalytic cracking catalysts different from those of the present application.

Comparative Example 1

2000 g of NaY molecular sieve (dry basis) was added to 20 liters of deionized water, stirred evenly, and 1000 g of $(NH_4)_2SO_4$ was added thereto, stirred, and heated to 90-95° C. for 1 hour. Then, the mixture was filtered and washed, and the filter cake was dried at 120° C., and then subjected to hydrothermal modification treatment by roasting at a temperature of 650° C. in a 100% steam atmosphere for 5 hours.

Then, the resultant was added to 20 liters of deionized water, stirred evenly, and 1000 g of $(NH_4)_2SO_4$ was added thereto, stirred, and heated to 90-95° C. for 1 hour. Then, after filtering and washing, the filter cake was dried at 120° C. and then subjected to a second hydrothermal modification treatment by roasting at a temperature of 650° C. in a 100% steam atmosphere for 5 hours, to obtain a hydrothermally ultra-stabilized Y-type molecular sieve free of rare earth that had undergone two stages of ion-exchange and two stages of hydrothermal ultra-stabilization, designated as DZ-1.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of DZ-1.

After DZ-1 was aged in a bare state at 800° C. for 17 hours in a 100% steam atmosphere, the crystallinity of the molecular sieve DZ-1 before and after aging was analyzed by XRD and the relative crystallinity retention after aging was calculated. The results are shown in Table 2.

The DZ-1 molecular sieve, kaolin, water, pseudo-boehmite binder, and aluminum sol were slurried, and spray-dried according to the method conventionally used for preparing a catalytic cracking catalyst, to obtain a microsphere catalyst, designated as DC-1 (see the method described in Example 1).

The DC-1 catalyst obtained comprised 30 wt % of DZ-1 molecular sieve, 42 wt % of kaolin, 25 wt % of pseudo-boehmite, and 3 wt % of aluminum sol.

Comparative Example 2

2000 g of NaY molecular sieve (dry basis) was added to 20 liters of deionized water, stirred evenly, and 1000 g of ($NH_4$)$_2SO_4$ was added thereto, stirred, and heated to 90-95° C. for 1 hour. Then, the mixture was filtered and washed, and the filter cake was dried at 120° C., and then subjected to hydrothermal modification treatment by roasting at a temperature of 650° C. in 100% steam atmosphere for 5 hours.

Then, the resultant was added to 20 liters of deionized water, stirred evenly, 200 ml of RE($NO_3$)$_3$ solution (the rare earth concentration calculated on the basis of $RE_2O_3$ in the $RECl_3$ solution was 319 g/L, and RE was mixed rare earth of La and Ce, with the mass ratio of $La_2O_3$:$Ce_2O_3$ calculated on the basis of rare earth oxides being 3:2) and 900 g ($NH_4$)$_2SO_4$ were added thereto, stirred and heated 90-95° C. for 1 hour. Then, after filtering and washing, the filter cake was dried at 120° C. and then subjected to a second hydrothermal modification treatment by roasting at a temperature of 650° C. in a 100% steam atmosphere for 5 hours, to obtain a hydrothermally ultra-stabilized Y-type molecular sieve containing rare earth that had undergone two stages of ion-exchange and two stages of hydrothermal ultra-stabilization, designated as DZ-2.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of DZ-2.

After DZ-2 was aged in a bare state at 800° C. for 17 hours in a 100% steam atmosphere, the crystallinity of the molecular sieve DZ-2 before and after aging was analyzed by XRD, and the relative crystallinity retention after aging was calculated. The results are shown in Table 2.

The DZ-2 molecular sieve, kaolin, water, pseudo-boehmite binder, and aluminum sol were slurried, and spray-dried according to the method conventionally used for preparing a catalytic cracking catalyst, to obtain a microsphere catalyst, designated as DC-2 (see the method described in Example 1).

The DC-2 catalyst obtained comprised 30% by weight of DZ-2 molecular sieve, 42% by weight of kaolin, 25% by weight of pseudo-boehmite, and 3% by weight of aluminum sol.

Comparative Example 3

2000 kg NaY molecular sieve (dry basis) was added to 20 $m^3$ of water, stirred evenly, 650 L of RE($NO_3$)$_3$ solution (the rare earth concentration calculated on the basis of $RE_2O_3$ in the $RECl_3$ solution was 319 g/L, and RE was mixed rare earth of La and Ce, with the mass ratio of $La_2O_3$:$Ce_2O_3$ calculated on the basis of rare earth oxides being 3:2) was added thereto, stirred, and heated to 90-95° C. for 1 hour, followed by filtering and washing.

The filter cake was sent to a flash roaster for roasting and drying at a controlled temperature of 500° C. in a dry air atmosphere for 2 hours, to obtain a water content of less than 1% by weight.

Then, the dried molecular sieve material was sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method described in Example 1 of the Patent Application Publication No. CN103787352A under the following conditions: the mass ratio of $SiCl_4$:Y-type molecular sieve was 0.4:1, the feed rate of the molecular sieve was 800 kg/h and the reaction temperature was 580° C.

The molecular sieve material obtained after the gas phase ultra-stabilization was separated by a gas-solid separator, sent to a secondary exchange tank containing 20 $m^3$ of water added in advance, and stirred evenly. The mass of the molecular sieve material added to the secondary exchange tank was 2000 kg (weight on a dry basis). After that, 1.2 $m^3$ of 5 wt % nitric acid was slowly added, heated to 95° C., and stirring was continued for 90 minutes; then, 90 kg of citric acid and 40 kg of oxalic acid were added, and stirring was continued at 93° C. for 70 minutes, followed by filtering, and washing.

After that, the molecular sieve cake was directly added to a solution containing ammonium phosphate, with the molecular sieve being added in an amount such that the mass ratio of phosphorus (on the basis of $P_2O_5$) to the molecular sieve was 0.015:1, and the mass ratio of water to the molecular sieve was 2.8:1, and the reaction was conducted at 70° C. for 30 min, followed by filtering, washing, and drying, to obtain a molecular sieve, designated as DZ-3.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of DZ-3.

After DZ-3 was aged in a bare state at 800° C. for 17 hours in a 100% steam atmosphere, the crystallinity of the molecular sieve DZ-3 before and after aging was analyzed by XRD, and the relative crystallinity retention after aging was calculated. The results are shown in Table 2.

The DZ-3 molecular sieve, kaolin, water, pseudo-boehmite binder, and aluminum sol were slurried, and spray-dried according to the method conventionally used for preparing a catalytic cracking catalyst, to obtain a microsphere catalyst, designated as DC-3 (see the method described in Example 1).

The DC-3 catalyst obtained comprised 30% by weight of DZ-3 molecular sieve, 42% by weight of kaolin, 25% by weight of pseudo-boehmite, and 3% by weight of aluminum sol.

Test Examples

The catalysts obtained in Examples 1-3 were evaluated for their micro-activity for light oils. The catalysts SC-1, SC-2 and SC-3 prepared in Examples 1-3 were each aged at 800° C. in a 100% steam atmosphere for 4 hours or 17 hours, and evaluated for their micro-activity for light oils. The evaluation results are shown in Table 3. The test examples corresponding to the catalysts SC-1, SC-2, and SC-3 are referred to as Test Example 1, Test Example 2, and Test Example 3, respectively.

Evaluation of Micro-Activity for Light Oils:

The micro-activity for light oils of each catalyst was evaluated according to the standard method of RIPP 92-90 (see "Petrochemical Analysis Methods (RIPP Test Methods)", edited by Cuiding YANG et al., Science Press, September 1990, pp. 263-268), in which the catalyst loading was 5.0 g, the reaction temperature was 460° C., and the feedstock oil was Dagang light diesel oil having a distillation range of 235-337° C. The composition of the product was analyzed by gas chromatography, and the micro-activity for light oils was calculated based on the composition of the product.

Micro-activity for light oils (MA)=(production of gasoline below 216° C.+gas production+coke production)/total amount of feed×100%.

Comparative Test Examples

The catalysts DC-1, DC-2 and DC-3 obtained in Comparative Examples 1-3 were each aged at 800° C. in a 100% steam atmosphere for 4 hours or 17 hours, and evaluated for their micro-activity for light oils. The evaluation method is shown in the Test Examples section, and the evaluation results are shown in Table 3. The comparative test examples corresponding to the catalysts DC-1, DC-2 and DC-3 are referred to as Comparative Test Example 1, Comparative Test Example 2, and Comparative Test Example 3, respectively.

Application Examples

The SC-1, SC-2 and SC-3 catalysts were aged at 800° C. in a 100% steam atmosphere for 12 hours, and then evaluated on a small fixed fluidized bed reactor (ACE) for the catalytic cracking performance for processing hydrogenated LCOs. Cracked gas and product oil were collected separately and analyzed by gas chromatography. The catalyst loading was 9 g, the reaction temperature was 500° C., and the weight hourly space velocity was 16 h$^{-1}$. The catalyst-to-oil mass ratios are shown in Table 5, the properties of the feedstock used in the ACE test are shown in Table 4, and the evaluation results are shown in Table 5. The application examples corresponding to the SC1, SC2, and SC3 catalysts are referred to as Application Example 1, Application Example 2, and Application Example 3, respectively.

Effective conversion rate of LCO/%=100−diesel oil yield−dry gas yield−coke yield−heavy oil yield.

Comparative Application Examples

The DC-1, DC-2, DC-3 catalysts and the HAC catalyst used in the working examples of Chinese Patent Application Publication No. CN 104560187A were aged at 800° C. in a 100% steam atmosphere for 12 hours, and then evaluated on a small fixed fluidized bed reactor (ACE) for the catalytic cracking performance for processing hydrogenated LCOs. The evaluation method is the same as that described in the Application Examples section. The properties of the feedstock used in the ACE test are shown in Table 4, and the evaluation results are shown in Table 5. The comparative application examples corresponding to the DC1, DC2, DC3 catalysts and the HAC catalyst are referred to as Comparative Application Example 1, Comparative Application Example 2, Comparative Application Example 3, and Comparative Application Example 4, respectively.

Effective conversion rate of LCO/%=100−diesel oil yield−dry gas yield−coke yield−heavy oil yield.

TABLE 1

Properties of molecular sieves obtained in Examples 1-3 and Comparative Examples 1-3

| | Ex. 1 | Ex. 2 | Ex. 3 | Comp. Ex. 1 | Comp. Ex. 2 | Comp. Ex. 3 |
|---|---|---|---|---|---|---|
| Name of molecular sieve | SZ-1 | SZ-2 | SZ-3 | DZ-1 | DZ-2 | DZ-3 |
| RE$_2$O$_3$ content/wt % | 5.8 | 8.6 | 6.3 | 0 | 2.7 | 6.2 |
| Na$_2$O content/wt % | 0.09 | 0.15 | 0.14 | 1.3 | 1.5 | 0.79 |
| P$_2$O$_5$ content/wt % | 3.53 | 2.86 | 1.39 | 0 | 0 | 1.38 |
| ZnO content/wt % | 1.0 | 2.0 | 4.0 | | | |
| Total SiO$_2$/Al$_2$O$_3$ molar ratio | 10.84 | 8.22 | 9.98 | 4.94 | 4.85 | 10.67 |
| Framework SiO$_2$/Al$_2$O$_3$ molar ratio | 11.95 | 8.79 | 10.87 | 10.39 | 7.83 | 11.39 |
| Framework aluminum/Total aluminum × 100 | 90.7 | 93.5 | 91.8 | 47.59 | 61.99 | 93.65 |
| Non-framework aluminum/Total aluminum × 100 | 9.3 | 6.5 | 8.2 | 52.41 | 38.01 | 6.35 |
| Lattice constant/nm | 2.442 | 2.45 | 2.445 | 2.446 | 2.453 | 2.444 |
| Crystallinity/% | 70.2 | 71.6 | 75.2 | 60.1 | 59.5 | 58.1 |
| Lattice collapse temperature/° C. | 1085 | 1067 | 1075 | 1038 | 1020 | 1047 |
| Specific surface area/(m$^2$/g) | 644 | 668 | 654 | 615 | 598 | 645 |
| Total pore volume/(mL/g) | 0.413 | 0.393 | 0.385 | 0.349 | 0.322 | 0.329 |
| Micropore volume/(mL/g) | 0.257 | 0.277 | 0.273 | 0.255 | 0.249 | 0.309 |
| Pore volume of secondary pores (2.0-100 nm)/(mL/g) | 0.156 | 0.116 | 0.112 | 0.094 | 0.073 | 0.020 |
| Percentage of pore volume of secondary pores having a pore size of 2.0-100 nm to total pore volume/% | 37.78 | 29.52 | 29.09 | 26.93 | 22.67 | 6.08 |
| Percentage of pore volume of secondary pores having a pore size of 8.0-100 nm to total pore volume of secondary pores (2.0-100 nm)/% | 75.15 | 68.17 | 59.73 | 18.35 | 16.24 | 1.15 |
| B acid/L acid (strong acid content ratio) | 4.51 | 5.37 | 4.93 | 0.52 | 0.83 | 2.67 |

It can be seen from Table 1 that the modified Y-type molecular sieve provided in the present application has the following advantages: a low sodium oxide content, a relatively lower non-framework aluminum content at a relatively higher silica-alumina ratio, a relatively higher percentage of the pore volume of secondary pores having a pore size of 2.0-100 nm to the total pore volume, a relatively higher B acid/L acid ratio (the ratio of strong B acid content to strong L acid content), a relatively higher crystallinity when the molecular sieve has a relatively smaller lattice constant and a relatively higher rare earth content, and a high thermal stability.

TABLE 2

Aging test of the molecular sieves obtained in Examples 1-3 and Comparative Examples 1-3

| Example No. | Name of molecular sieve | Relative crystallinity of fresh molecular sieve sample (%) | Relative crystallinity of aged molecular sieve sample (%) (800° C./aged for 17 hours) | Relative crystallinity retention/% |
|---|---|---|---|---|
| Ex. 1 | SZ-1 | 70.3 | 40.41 | 57.48 |
| Ex. 2 | SZ-2 | 71.8 | 37.31 | 51.96 |
| Ex. 3 | SZ-3 | 75.3 | 44.16 | 58.65 |
| Comp. Ex. 1 | DZ-1 | 60.1 | 4.30 | 7.15 |
| Comp. Ex. 2 | DZ-2 | 59.5 | 5.90 | 9.92 |
| Comp. Ex. 3 | DZ-3 | 58.1 | 21.01 | 36.16 |

It can be seen from Table 2 that, after being aged in a bare state under severe conditions at 800° C. for 17 hours, samples of the modified Y-type molecular sieve provided in the present application show a relatively higher relative crystallinity retention, which indicates that the modified Y-type molecular sieve provided in the present application has a high hydrothermal stability.

TABLE 3

Results of Test Examples 1-3 and Comparative Test Examples 1-3

| Example No. | Name of catalyst | MA (initial) (800° C./h) | MA (equilibrium) (800° C./17 h) | MA (equilibrium)/ MA (initial) |
|---|---|---|---|---|
| Test Ex. 1 | SC1 | 85 | 73 | 85.88 |
| Test Ex. 2 | SC2 | 86 | 71 | 82.56 |
| Test Ex. 3 | SC3 | 84 | 71 | 84.52 |
| Comp. Test Ex. 1 | DC1 | 41 | 18 | 43.90 |
| Comp. Test Ex. 2 | DC2 | 52 | 29 | 55.77 |
| Comp. Test Ex. 3 | DC3 | 80 | 59 | 73.75 |

TABLE 4

Properties of the hydrogenated LCO used in the Application Examples

| Item | Value |
|---|---|
| Carbon content/% | 88.91 |
| Hydrogen content/% | 11.01 |
| Density at 20° C. (kg/m$^3$) | 910.7 |
| Hydrocarbon composition (by mass), determined by mass spectrometry/% | |
| Paraffins | 10.1 |
| Total naphthenes | 16.9 |
| Total monocyclic aromatics | 60.3 |
| Total bicyclic aromatics | 11.5 |
| Tricyclic aromatics | 1.2 |
| Total aromatics | 73 |
| Colloid | 0 |
| Total weight | 100 |
| Nitrogen content, mg/L | 0.9 |
| Sulfur content, mg/L | 49 |

TABLE 5

Results of Application Examples 1-3 and Comparative Application Examples 1-4

| | Example No. | | | | | | |
|---|---|---|---|---|---|---|---|
| | Application Ex. 1 | Application Ex. 2 | Application Ex. 3 | Comp. Application Ex. 1 | Comp. Application Ex. 2 | Comp. Application Ex. 3 | Comp. Application Ex. 4 |
| Name of catalyst | SC-1 | SC-2 | SC-3 | DC-1 | DC-2 | DC-3 | HAC Catalyst |
| Name of molecular sieve | SZ-1 | SZ-2 | SZ-3 | DZ-1 | DZ-2 | DZ-3 | |
| Catalyst-to-oil ratio | 5 | 5 | 5 | 9 | 8 | 5 | 5 |
| Product distribution/wt % | | | | | | | |
| Dry gas | 1.18 | 1.38 | 1.13 | 2.25 | 2.37 | 2.09 | 2.6 |
| Liquefied gas | 17.92 | 17.3 | 17.21 | 10.17 | 10.87 | 14.35 | 11.3 |

TABLE 5-continued

Results of Application Examples 1-3 and Comparative Application Examples 1-4

|  | Application Ex. 1 | Application Ex. 2 | Application Ex. 3 | Comp. Application Ex. 1 | Comp. Application Ex. 2 | Comp. Application Ex. 3 | Comp. Application Ex. 4 |
| --- | --- | --- | --- | --- | --- | --- | --- |
| Coke | 1.23 | 1.22 | 1.01 | 4.46 | 4.65 | 3.1 | 3.9 |
| Gasoline | 57.49 | 57.06 | 58.02 | 45.24 | 45.78 | 46.83 | 45.1 |
| Diesel oil | 20.53 | 21.51 | 21.14 | 34.76 | 34.02 | 30.51 | 34.5 |
| Heavy oil | 1.65 | 1.53 | 1.49 | 3.12 | 2.31 | 3.12 | 2.6 |
| Total | 100 | 100 | 100 | 100 | 100 | 100 | 100 |
| BTX (benzene + toluene + xylene) yield in gasoline/wt % | 40.31 | 39.59 | 41.22 | 25.43 | 26.10 | 26.79 | 24.2 |
| Effective conversion rate of LCO/% | 75.41 | 74.36 | 75.23 | 55.41 | 56.65 | 61.18 | 56.4 |
| Total yield of ethylene + propylene/% | 6.45 | 6.31 | 6.13 | 3.25 | 3.48 | 4.32 | 3.62 |

As can be seen from Tables 3 and 5, as compared to the catalyst of the Comparative Examples, the catalytic cracking catalyst prepared using the molecular sieve provided in the present application as the active component shows a much higher hydrothermal stability, a significantly lower coke selectivity, a significantly higher gasoline yield, a significantly increased yield of BTX (i.e. benzene+toluene+xylene) in gasoline, and a significantly improved total yield of ethylene and propylene in the gas product obtained.

The preferred embodiments of the present application have been described in detail above, but the present application is not limited to the specific details in the above-described embodiments, and various modifications can be made to the technical solutions of the present application without departing from the inventive concept of the present application. All such modifications are intended to be covered by the present application.

It should be further noted that the specific technical features described hereinabove in particular embodiments may be combined in any suitable manner without contradiction. For brevity, those potential combinations are not described herein individually. In addition, any combination of the various embodiments of the present application may be made as long as it does not deviate from the spirit of the present application, and such combinations should also be regarded as a part of the disclosure of the present application.

The invention claimed is:

1. A modified Y molecular sieve, having a rare earth content of about 4% to about 11% by weight on the basis of rare earth oxide, a sodium content of no more than about 0.5% by weight on the basis of sodium oxide, a zinc content of about 0.5% to about 5% by weight on the basis of zinc oxide, and a phosphorus content of about 0.05% to about 10% by weight on the basis of phosphorus pentoxide, based on the weight of the modified Y molecular sieve on a dry basis, a framework silica-alumina ratio of about 7 to about 14 calculated on the basis of $SiO_2/Al_2O_3$ molar ratio, a percentage of non-framework aluminum content to the total aluminum content of no more than about 10%, and a percentage of the pore volume of secondary pores having a pore size of 2-100 nm to the total pore volume of about 20% to about 40%.

2. The modified Y molecular sieve according to claim 1, wherein the modified Y molecular sieve has one or more of the following characteristics:

a total pore volume of the modified Y molecular sieve of about 0.36 mL/g to about 0.48 mL/g;

a lattice constant of the modified Y molecular sieve of about 2.440 nm to about 2.455 nm;

a percentage of non-framework aluminum content to the total aluminum content of the modified Y molecular sieve of about 5% to about 9.5%;

a percentage of the pore volume of secondary pores having a pore size of 2-100 nm to the total pore volume of the modified Y molecular sieve of about 28% to about 38%;

a ratio of B acid to L acid in the strong acid content of the modified Y molecular sieve of no less than about 3.50, as determined by pyridine adsorption infrared spectroscopy at 350° C.;

a lattice collapse temperature of the modified Y molecular sieve of not lower than about 1060° C.;

a relative crystallinity of the modified Y molecular sieve of no less than about 60%; and/or a relative crystallinity retention of the modified Y molecular sieve of about 38% or more after being aged at 800° C. under atmospheric pressure in a 100 vol % steam atmosphere for 17 hours.

3. The modified Y molecular sieve according to claim 1, wherein the modified Y molecular sieve has a rare earth content of about 4.5% to about 10% by weight, a sodium content of about 0.05% to about 0.3% by weight, a phosphorus content of about 0.1% to about 6% by weight, based on the weight of the modified Y molecular sieve on a dry basis, a lattice constant of about 2.442 nm to about 2.451 nm, and a framework silica-alumina ratio of about 8.5 to about 12.6.

4. A method for catalytic cracking of hydrocarbon, comprising contacting a hydrocarbon feedstock with a catalytic cracking catalyst comprising a modified Y molecular sieve under catalytic cracking conditions, wherein the modified Y molecular sieve has a rare earth content of about 4% to about 11% by weight on the basis of rare earth oxide, a sodium content of no more than about 0.5% by weight on the basis of sodium oxide, a zinc content of about 0.5% to about 5% by weight on the basis of zinc oxide, and a phosphorus content of about 0.05% to about 10% by weight on the basis of phosphorus pentoxide, based on the weight of the modified Y molecular sieve on a dry basis, a framework silica-alumina ratio of about 7 to about 14 calculated on the basis of $SiO_2/Al_2O_3$ molar ratio, a percentage of non-framework aluminum content to the total aluminum content of no more than about 10%, and a percentage of the pore volume of secondary pores having a pore size of 2-100 nm to the total pore volume of about 20% to about 40%.

5. The method according to claim 4, wherein the hydrocarbon feedstock is a hydrogenated light cycle oil, and the catalytic cracking conditions include: a reaction temperature of about 500° C. to about 610° C., a weight hourly space velocity of about 2 $h^{-1}$ to about 16 $h^{-1}$, and a catalyst-to-oil weight ratio of about 3 to about 10.

6. A method for the preparation of a modified Y molecular sieve according, comprising the steps of:
(1) contacting a NaY molecular sieve with a rare earth salt solution for ion-exchange reaction to obtain an ion-exchanged molecular sieve;
(2) subjecting the ion-exchanged molecular sieve to a hydrothermal ultra-stabilization treatment to obtain a hydrothermally ultra-stabilized molecular sieve;
(3) subjecting the hydrothermally ultra-stabilized molecular sieve to a gas phase ultra-stabilization treatment by contacting and reacting with gaseous $SiCl_4$ to obtain a gas phase ultra-stabilized molecular sieve;
(4) subjecting the gas phase ultra-stabilized molecular sieve to an acid treatment by contacting with an acid solution to obtain an acid-treated molecular sieve;
(5) subjecting the acid-treated molecular sieve to phosphorus modification by contacting with a phosphorus compound to obtain a phosphorus-modified molecular sieve; and
(6) impregnating the phosphorus-modified molecular sieve with a zinc salt solution to obtain the modified Y molecular sieve,
wherein the modified Y molecular sieve has a rare earth content of about 4% to about 11% by weight on the basis of rare earth oxide, a sodium content of no more than about 0.5% by weight on the basis of sodium oxide, a zinc content of about 0.5% to about 5% by weight on the basis of zinc oxide, and a phosphorus content of about 0.05% to about 10% by weight on the basis of phosphorus pentoxide, based on the weight of the modified Y molecular sieve on a dry basis, a framework silica-alumina ratio of about 7 to about 14 calculated on the basis of $SiO_2/Al_2O_3$ molar ratio, a percentage of non-framework aluminum content to the total aluminum content of no more than about 10%, and a percentage of the pore volume of secondary pores having a pore size of 2-100 nm to the total pore volume of about 20% to about 40%.

7. The method according to claim 6, wherein the step (1) further comprises contacting a NaY molecular sieve with a rare earth salt in an aqueous solution for an ion-exchange reaction, wherein the ion-exchange reaction is conducted at a reaction temperature of about 15° C. to about 95° C., a reaction time of about 30 min to about 120 minutes, and a mass ratio of the NaY molecular sieve, the rare earth salt, and water of about 1:(0.01-0.18):(5-20), wherein the mass of the NaY molecular sieve is calculated on a dry basis, and the mass of the rare earth salt is calculated on the basis of rare earth oxide.

8. The method according to claim 6, wherein the hydrothermal ultra-stabilization treatment of the step (2) is carried out by roasting at a temperature of about 350° C. to about 480° C. in an atmosphere comprising about 30% to about 90% by volume of steam for about 4.5 h to about 7 h.

9. The method according to claim 6, wherein in the step (3), the reaction temperature is about 200° C. to about 650° C., the reaction time is about 10 minutes to about 5 hours, and the mass ratio of $SiCl_4$ to the hydrothermally ultra-stabilized molecular sieve is about (0.1-0.7):1, wherein the mass of the hydrothermally ultra-stabilized molecular sieve is calculated on a dry basis.

10. The method according to claim 6, wherein in the step (4), the acid treatment is carried out at a temperature of about 60° C. to about 100° C. for a period of about 1 hour to about 4 hours.

11. The method according to claim 10, wherein the acid comprises one or more of organic acids and inorganic acids, and wherein the mass ratio of the inorganic acid to the gas phase ultra-stabilized molecular sieve is about (0.001-0.05):1, and the mass ratio of the organic acid to the gas phase ultra-stabilized molecular sieve is about (0.02-0.10):1.

12. The method according to claim 11, wherein the organic acid is one or more selected from the group consisting of oxalic acid, malonic acid, succinic acid, methyl succinic acid, malic acid, tartaric acid, citric acid, and salicylic acid.

13. The method according to claim 11, wherein the inorganic acid is one or more selected from the group consisting of phosphoric acid, hydrochloric acid, nitric acid, and sulfuric acid.

14. The method according to claim 10, wherein the step (4) further comprises contacting and reacting the gas phase ultra-stabilized molecular sieve with an acid in an aqueous solution, wherein the mass ratio of the acid to the gas phase ultra-stabilized molecular sieve is about (0.001-0.15):1, the mass ratio of water in the aqueous solution to the gas phase ultra-stabilized molecular sieve is about (5-20):1, and the mass of the gas phase ultra-stabilized molecular sieve is calculated on a dry basis.

15. The method according to claim 6, wherein in the step (5), the phosphorus modification is conducted at a temperature of about 15° C. to about 100° C. for about 10 min to about 100 min.

16. The method according to claim 15, wherein the phosphorus compound used for the phosphorus modification is one or more selected from the group consisting of phosphoric acid, ammonium phosphate, ammonium dihydrogen phosphate, and diammonium hydrogen phosphate.

17. The method according to claim 6, wherein the step (6) further comprises subjecting the impregnated molecular sieve to calcination, wherein the impregnation temperature is about 10° C. to about 60° C., the calcination temperature is about 350° C. to about 600° C., and the calcination time is about 1 hour to about 4 hours.

18. A catalytic cracking catalyst, comprising, based on the weight of the catalyst on a dry basis, about 10% to about 50% by weight of a modified Y molecular sieve, a binder, and clay wherein the modified Y molecular sieve has a rare earth content of about 4% to about 11% by weight on the basis of rare earth oxide, a sodium content of no more than about 0.5% by weight on the basis of sodium oxide, a zinc content of about 0.5% to about 5% by weight on the basis of zinc oxide, and a phosphorus content of about 0.05% to about 10% by weight on the basis of phosphorus pentoxide, based on the weight of the modified Y molecular sieve on a dry basis, a framework silica-alumina ratio of about 7 to about 14 calculated on the basis of $SiO_2/Al_2O_3$ molar ratio, a percentage of non-framework aluminum content to the total aluminum content of no more than about 10%, and a percentage of the pore volume of secondary pores having a pore size of 2-100 nm to the total pore volume of about 20% to about 40%.

19. The catalytic cracking catalyst according to claim 18, wherein the catalyst comprises about 10% to about 50% by weight of the modified Y molecular sieve, and about 10% to about 40% by weight of a binder and about 10% to about 80% by weight of clay, based on the weight of the catalyst on a dry basis.

20. The method according to claim 19, wherein the clay is selected from the group consisting of kaolin, hydrated halloysite, montmorillonite, diatomaceous earth, halloysite, saponite, rector, sepiolite, attapulgite, hydrotalcite, bentonite, and any combination thereof; and the binder is an alumina binder selected from the group consisting of alumina, hydrated alumina, aluminum sol, and any combination thereof, and the content of the binder is calculated on the basis of alumina.

* * * * *